(12) United States Patent
Jacobs et al.

(10) Patent No.: US 6,660,767 B2
(45) Date of Patent: Dec. 9, 2003

(54) COUMARIN COMPOUNDS AS MICROTUBULE STABILIZING AGENTS AND THERAPEUTIC USES THEREOF

(75) Inventors: Robert S. Jacobs, Santa Barbara, CA (US); Leslie Wilson, Santa Barbara, CA (US); Hamta Madari, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/060,317

(22) Filed: Feb. 1, 2002

(65) Prior Publication Data

US 2002/0151560 A1 Oct. 17, 2002

Related U.S. Application Data

(60) Provisional application No. 60/283,366, filed on Apr. 13, 2001, and provisional application No. 60/265,576, filed on Feb. 2, 2001.

(51) Int. Cl.$^7$ .............................................. A61K 31/35
(52) U.S. Cl. ........................................ 514/457; 514/28
(58) Field of Search ................................... 514/457, 28

(56) References Cited

U.S. PATENT DOCUMENTS

| | | | |
|---|---|---|---|
| 5,580,898 A | | 12/1996 | Trojanowski et al. |
| 5,716,982 A | * | 2/1998 | Han et al. ................. 514/457 |
| 5,783,599 A | * | 7/1998 | Kun et al. ................. 514/457 |
| 6,004,978 A | * | 12/1999 | Kun et al. ................. 514/309 |
| 6,331,562 B1 | * | 12/2001 | Bhagwat et al. ........... 514/457 |
| 2002/0165210 A1 | * | 11/2002 | Agata et al. .............. 514/171 |

OTHER PUBLICATIONS

Dulal Panda et al., "Differential Effects of Vinblastine on Polymerization and Dynamics at Opposite Microtubule Ends", The Journal of Biological Chemistry, vol. 271, No. 47, (1996), pp. 29807–29812.

Panda et al., "Antiproliferative Mechanism of Action of Cryptophycin–52: Kinetic Stabilization of Microtubule Dynamics by High–Affinity Binding to Microtubule Ends", PNAS USA, vol. 95, Issue 16, (1998), pp. 9313–9318.

Dulal Panda et al., "Stabilization of Microtubule Dynamics by Estramustine by Binding to a Novel Site in Tubulin: A Possible Mechanistic basis for its Antitumor Action", PNAS USA vol. 94, (1997), pp. 10560–10564.

Dulal Panda et al., "Suppression of Microtubule Dynamics by LY290181", The Journal of Biological Chemistry, vol. 272, No. 12, (1997), pp. 7681–7687.

Dulal Panda et al., "Kinetic Stabilization of Microtubule Dynamics at Steady State in Vitro by Substoichiometric Concentrations of Tubulin–Colchicine Complex", Biochemistry, vol. 34, (1995), pp. 9921–9929.

M. Podbielkowska et al., "Effect of Coumarin and its Derivatives on Mitosis and Ultrastructure of Meristematic Cells", International Journal of Pharmacognosy, vol. 33, No. 1, (1995), pp. 7–15.

Eric K. Rowinsky, M.D., et al., Paclitaxel (TAXOL), The New England Journal of Medicine, vol. 332, No. 15. (1995), pp. 1004–1014.

Dan Sackett et al., "Taxanes", Cancer Chemotherapy and Biological Response Modifiers, Annual 17, pp. 50–79.

William W. Saxton et al., "Tubulin Dynamics in Cultured Mammalian Cells", The Journal of Cell Biology, vol. 99, (1984), pp. 2175–2186.

Andrew D. Seidman et al., "Estramustine and Vinblastine: Use of Prostate Specific Antigen as a Clinical Trial End Point for Hormone Refractory Prostatic Cancer", The Journal of Urology, vol. 147, (1992), pp. 931–934.

R.A. Walker et al., "Dynamic Instability of Individual Microtubules Analyzed by Video Light Microscopy: Rate Constants and Transition Frequencies", The Journal of Cell Biology, vol. 107, (1988), pp. 1437–1448.

Leslie Wilson et al., "Microtubule Dynamics: Taking Aim at a Moving Target", Chemistry & Biology, vol. 2, (1995), pp. 569–573.

Leslie Wilson et al., "Kinetics and Steady State Dynamics of Tubulin Addition and Loss at Opposite Microtubule Ends: The Mechanism of Action of Colchicine", Annals New York Academy of Science, pp. 690–708.

Zobel et al., Pharmaceutical Biology, vol. 38, No. 3, (2000), pp. 192–196.

Gary R. Hudes et al., "Phase II Study of Estramustine and Vinblastine, Two Microtubule Inhibitors, in Hormone–Refractory Prostate Cancer", Journal of Clinical Oncology, vol. 10, No. 11, (1992), pp. 1754–1761.

Roberts S. Jacobs et al., "Fertilized Sea Urchin Eggs as a Model for Detecting Cell Division Inhibitors", Detecting Cell Division Inhibitors. pp. 481–493.

Mary Ann Jordan et al., "Effects of Vinblastine, Podophyllotoxin and Nocodazole on Mitotic Spindles/Implications for the Role of Microtubule Dynamics in Mitosis", Journal of Cell Science, vol. 102, (1992), pp. 401–416.

Mary A. Jordan, "Mechanism of Inhibition of Cell Proliferation by Vinca Alkaloids", Cancer Research, vol. 51, (1991), pp. 2212–2222.

Joso et al., Biochem, vol. 32, No. 5, (1993), pp. 1285–1293.

A.M. Keightley et al., "Coumarin and its 4— and 7—Substituted Derivatives as Retardants of Mitoses in Allium Root Promeristem", International Journal of Pharmacognosy, vol. 34, No. 2, (1996), pp. 105–113.

(List continued on next page.)

Primary Examiner—James H. Reamer
(74) Attorney, Agent, or Firm—Jacobson Holman PLLC; Suzannah K. Sundby

(57) ABSTRACT

Compounds and compositions for stabilizing microtubules are disclosed. Also disclosed are methods of inhibiting, preventing, regulating, modulating, attenuating, stabilizing, or affecting microtubule formation or function. Methods of treating, preventing or inhibiting diseases and disorders associated with microtubule formation, function, or both by administering a microtubule stabilizing agent such as coumarin is also disclosed.

23 Claims, 12 Drawing Sheets

OTHER PUBLICATIONS

R.J. Kowalski et al., vol. 26, No. 4, (1993), pp. 282–290.

James C. Lee et al., "Interaction of Vinblastine with Calf Brain Microtubule Protein", The Journal of Biological Chemistry, vol. 250, No. 24, (1975), pp. 9276–9282.

M. Earnest Marshall, "Treatment of Advanced Malignant Melanoma with Coumarin and Cimetidine: A Pilot Study", Cancer Chemother Pharmacol, vol. 24, (1989), pp. 65–66.

M.E. Marshall et al., "Growth–Inhibitory Effects of Coumarin (1,2–Benzopyrone) and 7–Hydroxycoumarin on Human Malignant Cell Lines in Vitro", J. Cancer Res. Clin. Oncol., vol. 120 (Suppl), (1994), pp. S3–S10.

D. Menzel et al., "Coumarins in the Siphonalean Green Algal Family Dasycladaceae Kutzing (Chlorophyceae", Botanica Marina, vol. XXVI, (1983), pp. 23–29.

E.T. O'Brien et al., "Selective Inhibition of Cytokinesis in Sea Urchin Embryos by Low Concentrations of Stypoldione, a Marine Natural Product that Reacts with Sulfhydryl Groups", Molecular Pharmacology, vol. 35, (1989), pp. 635–642.

Richard O'Kennedy et al., Coumarins, Biology Applications and Mode of Action, John Wiley & Sons (England) ed. O'Kennedy and Thornes (1997).

Panda et al., PNAS USA, vol. 91, No. 24, (1994), pp. 11358–11362.

Dulal Panda et al., "Rapid Treadmilling of Brain Microtubules Free of Microtubule–Associated Proteins in Vitro and its Suppression by Tau", PNAS USA vol. 96, No. 22, (1999), pp. 12459–12464.

Balczon et al., Cell Motility, vol. 3 (1983), pp. 213–226.

Cox et al., Human Toxicology, vol. 8, No. 6, (1989), pp. 213–226.

Pierre Dustin, "They are Structural Organelles that are found in all Nucleated Cells. Assembled like Scaffolding from Protein Subunits, they participate in Cell Division, Cell Movement and the Maintenance of Cell Shape", Microtubules, pp. 67–76.

Denise Egan et al., "Pharmacology, Metabolism, Analysis, and Applications of Coumarin and Coumarin–Related Compounds", Drug Metabolism Reviews, vol. 22, No. 5, (1990), pp. 503–529.

Farrell et al., Biochem, vol. 23, (1984), pp. 3741–3748.

Kevin W. Farrell et al., "Phase Dynamics at Microtubule Ends: The Coexistence of Microtubule Length Changes and Treadmilling", The Journal of Cell Biology, vol. 104, (1987), pp. 1035–1046.

A. Gawron et al. "Cytostatic Activity of Coumarins in Vitro", Planta Med. (1987), pp. 526–529.

John H. Hayden et al., "Kinetochores Capture Astral Microtubules During Chromosome Attachment to the Mitotic Spindle: Direct Visulaization in Live Newt Lung Cells", The Journal of Cell Biology, vol. 111, (1990), pp./ 1039–1045.

Peter J. Hollenbeck et al., "Microtubule Distribution and Reorganization in the First Cell Cycle of Fertilized Eggs of *Lytechinus pictus*", European Journal of Cell Biology, vol. 37, (1985), pp. 140–148.

J.R.S. Hoult et al., "Pharmacological and Biochemical Actions of Simple Coumarins: Natural Products with Therapeutic Potential", Gen. Pharmac., vol. 27, No. 4, (1996), pp. 713–722.

Gary R. Hudes et al., "Phase II Trial of 96–Hour Paclitaxel Plus Oral Estramustine Phosphate in Metastatic Hormone–Refractory Prostate Cancer", Journal of Clinical Oncology, vol. 15, No. 9 (1997), pp. 3156–3163.

Kawaii, et al. (2001) "Antiproliferative Effect of Isopentenylated Coumarins on Several Cancer Cell Lines" Anticancer Research 21(3B):1905–1911. Abstract.

Podbielkowska, et al. (1995) "Effect of Coumarin and its Derivatives on Mitosis and Ultrastructure of Meristematic Cells" International Journal of Pharmacology 33(1):7–15. Abstract.

* cited by examiner

COUMARIN COMPOUNDS AS MICROTUBULE STABILIZING AGENTS AND THERAPEUTIC USES THEREOF

CROSS REFERENCE TO RELATED APPLICATIONS

This application claims the benefit of U.S. Provisional Patent Application No. 60/283,366 filed Apr. 13, 2001, and U.S. Provisional Patent Application No. 60/265,576 filed Feb. 2, 2001, both of which name Robert S. Jacobs, Leslie Wilson, and Hamta Madari as co-inventors and are herein incorporated by reference.

STATEMENT REGARDING FEDERALLY SPONSORED RESEARCH OR DEVELOPMENT

This invention was made with Government support under Grant No. R/MP-81, awarded by the National Oceanic & Atmospheric Administration (NOAA) California Sea Grant. The Government has certain rights in this invention.

BACKGROUND OF THE INVENTION

1. Field of the Invention

The present invention generally relates to microtubule stabilizing agents and methods of using thereof. Specifically, the present invention relates to coumarin compounds as microtubule stabilizing agents.

2. Description of Related Art

Microtubules, present in all eukaryotic cells, are required for normal cellular activities such as cell division, motility, anchorage, transport between cellular organelles, extracellular secretory processes, modulation of growth factor interactions with cell surface receptors and intracellular signal transduction. See Dustin, P. (1980) Sci. Am. 243:66–76. Microtubules are in dynamic equilibrium with their soluble protein subunits, $\alpha$ and $\beta$ tubulin heterodimers.

These dynamic protein fibers are essential for cell division. During cell division, the cell must duplicate its DNA and internal components and separate them to form the two nuclei in the daughter cells. The cell then splits into two new daughter cells when these new nuclei have separated. Mitosis is the process during cell reproduction in which ordering and relocation of replicated genetic material occurs and the chromosomes are partitioned equally between two new cells. When cells enter mitosis, the microtubule network is broken down and a bipolar microtubule spindle is assembled from the centrosome. Microtubules from the spindle attach to the chromosomes and move them to the spindle poles. Dynamic instability, the rapid growing and shortening of microtubules, is responsible for the partitioning of chromosomes. These rapid dynamics are highly sensitive to antimitotic drugs. Many substances, derived from natural products, bind to tubulin or microtubules and inhibit cell proliferation by acting on spindle microtubules. Microtubules are thus, intimately involved with cell replication; if the microtubules in a tumor cell can be prevented from forming, the chromosomes cannot be partitioned, the cell cannot replicate and the tumor is unable to grow.

Various diseases and disorders are associated with microtubule assembly, disassembly, function or a combination thereof. For example, diseases and disorders associated with cell proliferation such as cancer, fungal diseases such as candida and aspergillus, cysts, neurodegenerative diseases and disorders such as Alzheimer's disease, ALS, Pick's and various forms of Parkinson's, gout, malaria, atherosclerosis, restenosis, chronic inflammation, rheumatoid arthritis, psoriasis, diabetic retinopathy, and the like are associated with microtubule function.

Several agents which affect microtubule assembly, disassembly and function are known and include, vinblastine, vincristine, colchicine, allocochicine, thiocolchicine, paclitaxel (Taxol®), maytansine, rhizoxin, trityl cysteine, epothilone, discodermolide, estramustine, nocodazole, taxotere® (docetaxel) and the like. Most of these agents destabilize or disassemble microtubules which is undesirable for treating diseases and disorders relating to the abnormal destabilization or disassembly of microtubules such as Alzheimer's disease.

However, taxol promotes the formation of microtubules and inhibits the normal dynamic reorganization of microtubules required for mitosis and cell proliferation. See Schiff, P. B., et al. (1979) Nature 277:665 and Schiff, P. B., et al. (1981) Biochemistry 20:3247. Taxol kinetically stabilizes microtubule dynamics by binding along the length of the microtubules without directly altering the cap. See Wilson, L. et al. (1985) Chemistry & Biology 2:569–573; Derry et al. (1995) Biochemistry 34(7):2203–2211. Thus, taxol has been shown to be efficacious against drug-refractory tumors such as ovarian and mammary gland tumors. See Hawkins, (1992) Oncology 6:17–23, Horwitz (1992) Trends Pharmacol. Sci. 13:134–146, and Rowinsky (1990) J. Nat'l Cancer Inst. 82:1247–1259. Unfortunately, several allergic reactions have been observed following administration of taxol. See Weiss, R. B., et al. (1990) J. Clin. Oncol. 8:1263. Additionally, cardiac arrhythmia and sinus bradycardia are associated with taxol administration in about 5% and about 40%, respectively, of patients. Furthermore, taxol is a cytotoxic agent and is toxic in large doses, over long periods of time, or both.

Therefore, a need exists for microtubule stabilizing agents which are less toxic as compared to taxol and taxol-like compounds for treating, preventing or inhibiting diseases and disorders associated with microtubule formation or function.

SUMMARY OF THE INVENTION

The present invention generally relates to coumarin compounds and derivatives thereof.

In some embodiments, the present invention provides a method of stabilizing or modulating microtubules in a subject comprising administering at least one coumarin compound or a derivative thereof to the subject. The subject may be a cell or an organism. Preferably, the subject is mammalian, more preferably, the subject is human.

In preferred embodiments, the coumarin compound is coumarin, dicoumarol, 7-hydroxycoumarin (umbelliferone), 6,7-dihydroxycoumarin (esculetin), 3,6,7 trihydroxy coumarin, warfarin, or warfarin sodium (coumadin).

In some embodiments, the present invention provides a pharmaceutical composition comprising at least one coumarin compound or a pharmaceutically acceptable salt or prodrug thereof, at least one supplementary compound and a pharmaceutically acceptable excipient. The supplementary compound may be an antineoplastic agent, an antiproliferative agent, an anti-inflammatory agent, or an anti-fungal agent. Preferably, the supplementary compound is taxol, estramustine, taxotere, vinblastine, vincristine, discodermolide, griseofulvin, or amphotericin B.

In some embodiments, the present invention provides a method of treating, preventing or inhibiting a disease or disorder associated with microtubule formation or microtubule function in a subject comprising administering to the subject a therapeutically effective amount of at least one coumarin compound or a derivative thereof. In preferred embodiments, the disease or disorder is a hyperproliferative or cystic disease. More preferably, the disease or disorder is cancer, Alzheimer's disease, atherosclerosis, restenosis, or gout. An antineoplastic agent, an antiproliferative agent, an anti-inflammatory agent, or an anti-fungal agent may also be administered.

In some embodiments, the present invention provides a method of modulating a cell cycle of a cell comprising administering at least one coumarin compound or a derivative thereof to the cell.

In some embodiments, the present invention provides a method of treating, preventing or inhibiting cancer in a subject comprising administering to the subject a therapeutically effective amount of at least one coumarin compound or a derivative thereof and at least one antineoplastic agent. Preferably, the antineoplastic agent is taxol, estramustine, taxotere, vinblastine, vincristine, or discodermolide.

In some embodiments, the present invention provides a method of treating, preventing or inhibiting cancer in a subject comprising administering to the subject a therapeutically effective amount of at least one coumarin compound. Where only one coumarin compound is administered, the coumarin compound is not coumarin, 7-hydroxycoumarin, warfarin, or warfarin sodium.

The present invention also provides a kit for treating, preventing or inhibiting a disease or disorder associated with microtubule formation or microtubule function in a subject comprising at least one dose of at least one coumarin compound packaged together with at least one dose of an antineoplastic agent, an antiproliferative agent, an anti-inflammatory agent, or an anti-fungal agent. The kit may further comprise instructions for use, a drug delivery device such as a hypodermic needle, or both.

It is to be understood that both the foregoing general description and the following detailed description are exemplary and explanatory and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DESCRIPTION OF THE DRAWINGS

This invention is further understood by reference to the drawings wherein.

DETAILED DESCRIPTION OF THE INVENTION

Figure 1:
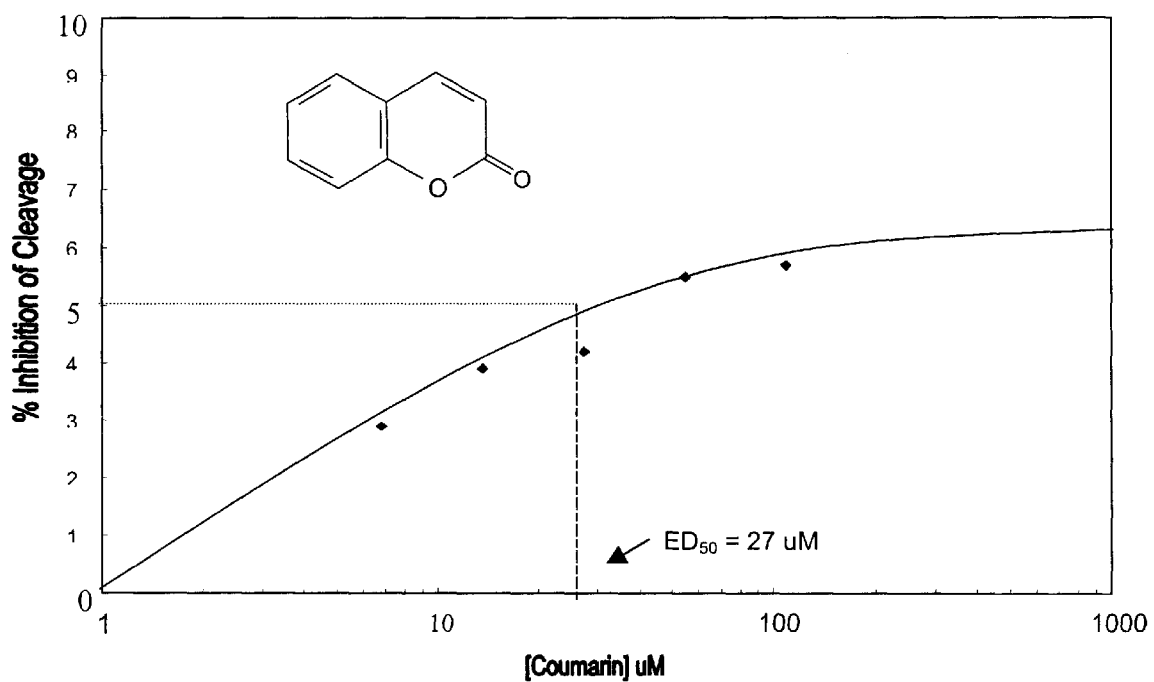
FIG. 1 shows the inhibition of S. purpuratus cell division by coumarin.
Figure 2:
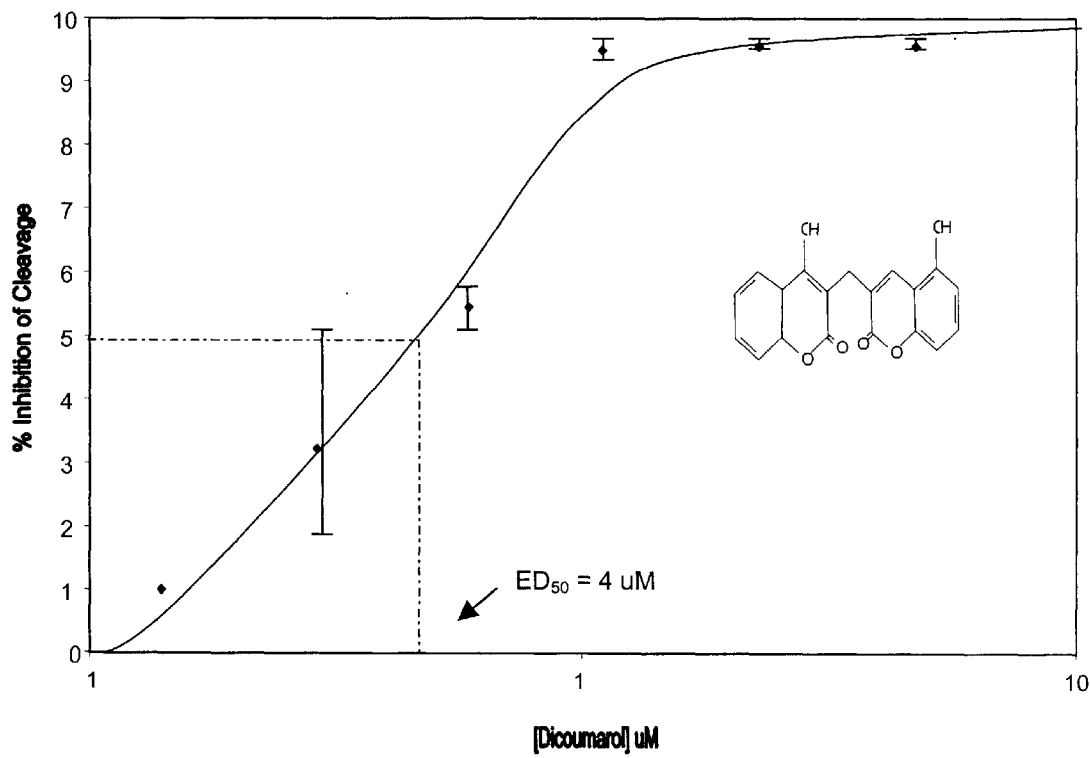
FIG. 2 shows the inhibition of S. purpuratus cell division by dicoumarol.
Figure 3:
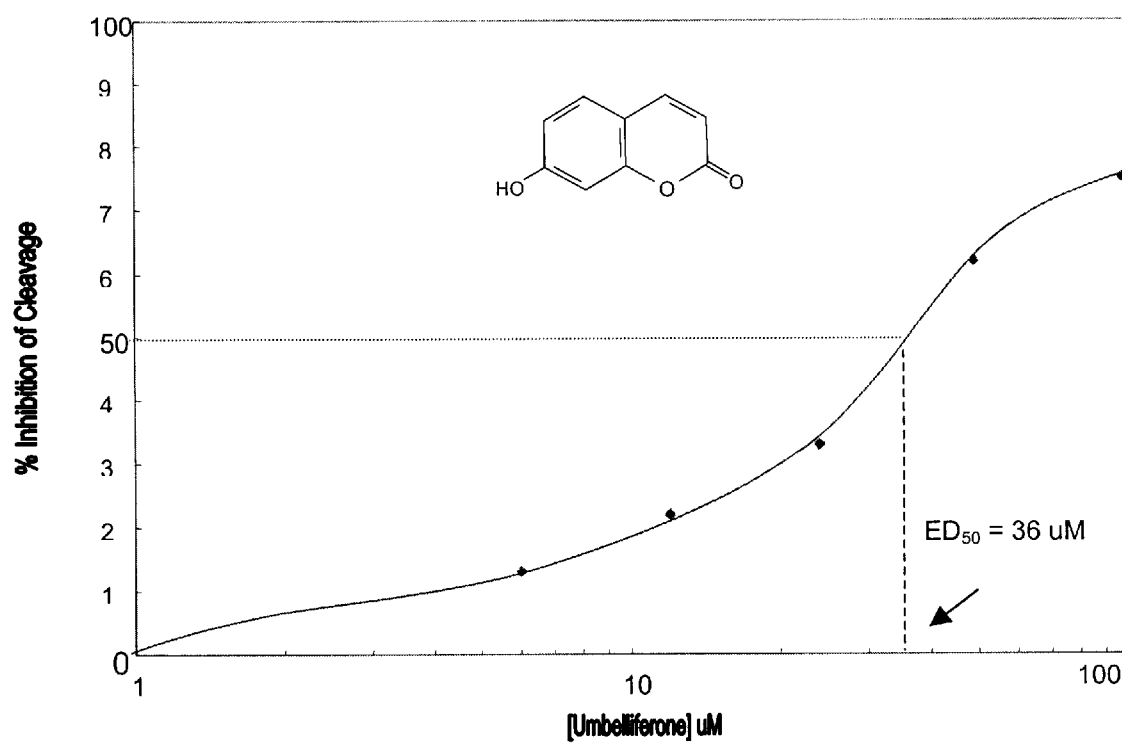
FIG. 3 shows the inhibition of S. purpuratus cell division by 7-hydroxycoumarin
Figure 4:
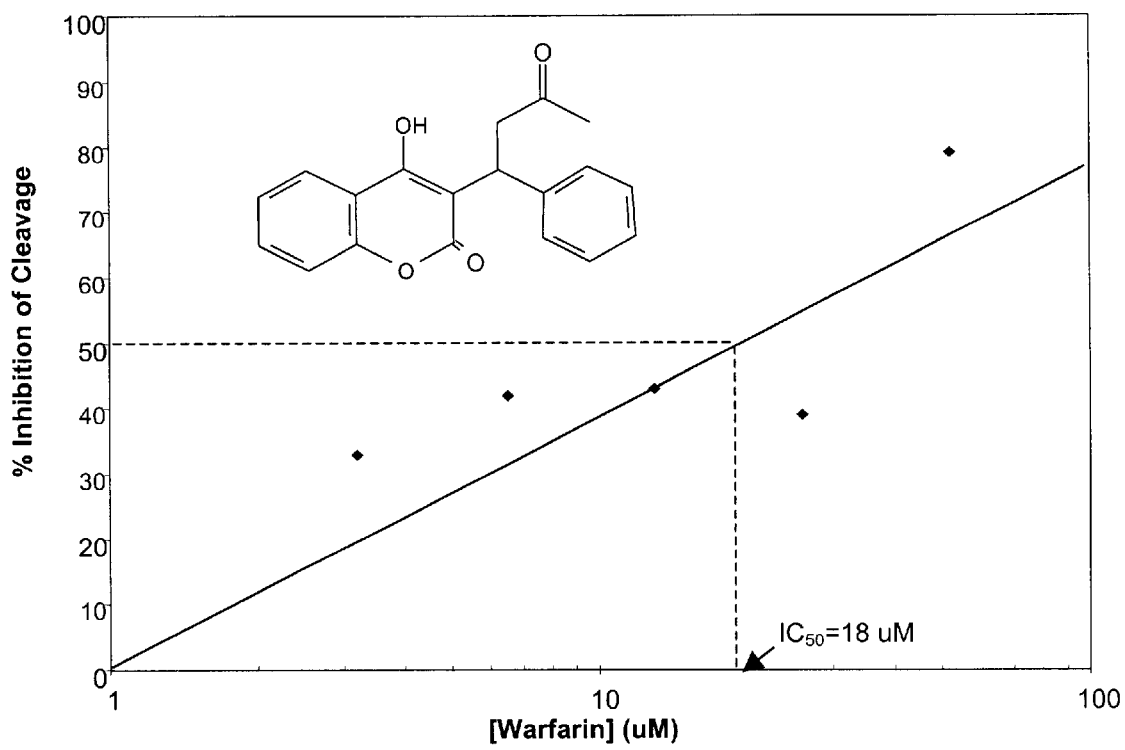
FIG. 4 shows the inhibition of S. purpuratus cell division by warfarin sodium.

Recently, coumarin compounds have been discovered to inhibit, prevent, or modulate microtubule disassembly, stimulate tubulin polymerization or microtubule assembly, or a combination thereof. Therefore, the present invention provides methods of modulating microtubule formation, function, or a combination thereof. The present invention also provides methods for treating, preventing, or inhibiting diseases and disorders related to microtubule formation, function, or both. Diseases and disorders related to microtubule formation, function, or both include cancer, fungal diseases such as candida and aspergillus, cysts, Alzheimer's disease, gout, malaria, atherosclerosis, restenosis, chronic inflammation, rheumatoid arthritis, psoriasis, diabetic retinopathy, chronic obstructive pulmonary disorder, tuberculosis, chronic cholecystitis, osteoarthritis, rheumatic carditis, bronchiectasis, Hashimoto's thyroiditis, and the like. As used herein, the phrases "associated with" or "related to" refer to diseases and disorders that may be treated, prevented, or inhibited by affecting or modulating microtubule formation, function, or a combination thereof.

Except for the taxanes, which also enhance microtubule polymerization, most of the well-studied anti-mitotic agents, e.g., colchicine, vinca alkaloids, cryptophycins, inhibit microtubule assembly at high concentrations. See Wilson et al. (1995) Chemistry & Biology 2:569–573, which is herein incorporated by reference. Taxol acts by binding directly to a microtubule along its length to stabilize it and also causes the soluble tubulin to assemble into microtubules.

Anti-mitotic agents that interact with tubulin protein are of interest because of their potential uses in the treatment of human neoplastic and inflammatory diseases. The clinical success of agents that prevent polymer disassembly (paclitaxel and docetaxel) has increased interest in drugs with a similar mechanism of action. See Rwoinsky and Donehower, (1995) N. Engl. J. Med. 332(15):1004–1014, which is herein incorporated by reference. While the effects of dicoumarol are similar to taxol, the molecular details of its association with tubulin are unique. Both compounds stabilize microtubule dynamics by significantly suppressing the shortening rate, increasing the time spent in attenuation, reduce catastrophe frequency, and have no significant affect on the growing rate. These stable microtubules are unable to depolymerization, and thus disrupt the normal dynamic organization of microtubules required for mitosis and cell division. However, a notable difference in the action of dicoumarol on microtubule as compared with taxol is that taxol binds preferentially to microtubules rather than tubulin dimers (Sackett and Fojo, (1997) Cancer Chemother. Biol. Response Modif. 17:59–79, which is herein incorporated by reference) while dicoumarol binds to free tubulin subunits. In addition, taxol effectively nucleates and enhances microtubule assembly, while dicoumarol does not. This indicates a different mechanism of action of dicoumarol in stabilizing microtubules from taxol that may prove useful in formulating combination therapy approaches.

Recent clinical trials have indicated that combinations of known antimitotic drugs result in increase antitumor activity and decreased toxicity. See Hudes et al. (1997) J. Clin. Oncol. 15(9):3156–3163; Hudes et al. (1992) J. Clin Oncol. 10(11):1754–1761; and Seidman et al., (1992) J. Urol. 147(3 Pt 2):931–934, which are herein incorporated by reference. Combination therapy with drugs that stabilize microtubule dynamics by different mechanisms may improve responses and minimize side effects of the individual drugs even further. This is supported by a study finding that the combination of paclitaxel with coumarin on meristematic cells of *Allium sativum* root tips increased anti-mitotic activity and was associate with fewer cytotoxic and clastogenic effects than when using paclitaxel alone. See Zobel and Schellenberger (2000) Pharmaceutical Biology 38(3):192–196, which are herein incorporated by reference. The increased anti-mitotic activity of the combination of paclitaxel and coumarin suggests that these agents may work synergistically and have the potential to be used as chemotherapeutic agents. Because of coumarin has a low toxicity and simple chemical structure, coumarin compounds may be combined with other chemotherapeutic and/or biological agents to improve on efficacy of various therapies where anti-mitotic activity is desired. Thus, combinations of at least one coumarin compound with other microtubule stabilizing agents are clinically desirable.

As described herein, although the coumarin compounds also stabilize microtubules and enhance microtubule assembly reactions, it is believed that coumarin compounds act on microtubules in a manner different from any other known microtubule-targeted drug. Therefore, coumarin compounds represent a new class of compounds that stabilize microtubules and enhance microtubule assembly reactions.

Coumarin compounds are naturally occurring organic compounds belonging to benzopyrones which comprise a benzene ring joined to a pyrone. See COUMARINS: BIOLOGY, APPLICATIONS AND MODE OF ACTION. Eds. O'Kennedy and Thornes, John Wiley & Sons, NY (1997), which is herein incorporated in its entirety. As used herein, coumarin compounds of the present invention are benzo-α-pyrones or compounds comprising a benzene ring joined to α-pyrone. Coumarin compounds are commonly found in a wide range of plants. The coumarin compound biosynthetic pathways vary in many plants and microorganisms and include the shikimic-phenylalanine pathway, the polyketide pathway and the hydroxycinnamate pathway. Coumarin compounds are also metabolized differently among various species. For example, the major metabolic pathway in humans is 7-hydroxylation which is catalyzed by CYP2A6, a cytochrome P450 enzyme and in the rat, hepatic 7-hydroxylation is almost absent.

Coumarin is a simple molecule and many of its derivatives have been reported to prevent disease, modulate growth and defense systems but their role in plant and animal biology has not been fully exploited. Unlike taxol, coumarin compounds, such as 7-hydroxycoumarin, have a low toxicity. See Cox et al. (1989) Human Toxicology 8(6):501–506; Egan, D. et al. (1990) Drug Metab. Rev. 22:503–529; Marshall, M. E. et al (1989) Cancer Chemother. Pharmacol. 24:65–66, which are herein incorporated by reference. For example, as disclosed herein, the coumarin compounds are found to be not as potent, or not as toxic, as taxol-like compounds. Therefore, coumarin compounds may be used in place of or in combination with taxol and other agents which affect microtubule formation, function, or both to treat, prevent, or inhibit diseases and disorders related to microtubule formation or function. Coumarin compounds may be used as adjuvant therapies for treating, preventing or inhibiting cancer and other proliferative diseases and disorders.

Additionally, as the period of taxol therapy is limited by the toxicity of taxol, extended periods of treatment may be obtainable with smaller doses of taxol in conjunction with the administration of a coumarin compound. Therefore, a subject suffering from a disease or disorder associated with microtubule formation or function which is normally treated with a given compound that is toxic to the subject at a given amount over given period of time may be treated with a coumarin compound and a smaller dose of the given compound over the given period of time or longer or the coumarin compound and the same dose of the given compound for a shorter period of time.

For example, a subject suffering from cancer, is normally treated with about 400 mg to about 7,000 mg daily of taxol per kg body weight about once every two or three weeks. The taxol dosages of subjects who experience severe neutropenia or neuropathy are generally reduced by about 20%. A subject being treated with a reduced amount of taxol may also be administered an amount of a coumarin compound, such as dicoumarol, wherein the combination of taxol and the coumarin compound provides a therapeutic effect similar to that provided with the normal amount of taxol alone. Alternatively, a subject may be treated more than once every two or three weeks with a reduced amount of taxol in combination with a coumarin compound. The subject may be treated with both taxol and the coumarin compound over a period of time that is longer than the prescribed treatment period for normal dosages of taxol alone. Therefore, a chronic disease such as cancer may be treated with an anti-neoplastic agent, such as taxol, and a coumarin compound over a period of time ranging from about a day to an extended period of time such as the life of the subject.

In methods wherein a subject suffering from cancer is or was being treated with conventional chemotherapy, is to be administered a coumarin compound, the coumarin compound is preferably one that does not exhibit anticoagulant properties, but does inhibit, prevent, regulate, modulate, attenuate, stabilize, or affect microtubule formation or function such as 7-hydroxycoumarin.

In preliminary studies of the anti-mitotic characteristics of coumarin compounds, several coumarin compounds, coumarin, dicoumarol, 7-hydroxycoumarin, and warfarin, inhibited the first cleavage of *S. purpuratus* embryos. See FIGS. 1–4. The concentrations required for half maximal inhibition of cleavage range from about 4 $\mu$M of dicoumarol to about 40 $\mu$M of 7-hydroxycoumarin. See FIGS. 1–4. These studies indicated that the coumarin compounds may inhibit cell division by acting on the microtubules which are critical for the first mitotic division.

The fertilized sea urchin egg is a useful experimental model for studying the mechanisms of drug action. Eggs fertilized at the same time undergo numerous highly synchronous divisions (generally much better than drug induced mammalian cell cultures), thereby allowing the rapid identification of drug-induced delays in cell cycle progression. Additionally, the first cell cycle in the sea urchin culture system exhibits a remarkable degree of pharmacological selectivity to mitotic spindle poisons while being relatively insensitive to agents acting by other common inhibitory mechanisms.

In order to determine if dicoumarol exerted its activity within any particular portion of the cell cycle, sea urchin embryos were exposed to dicoumarol at progressively later times after fertilization. This method may be used to identify any cell cycle phases that are either sensitive or insensitive to coumarin compounds. The ability of dicoumarol to block cells in mitosis, like a mitotic spindle poison, was examined. The first mitosis typically occurs between about 70 to about 90 minutes after fertilization and cytokinesis is usually complete at about 120 minutes, giving rise to two blastomeres. By adding dicoumarol to fertilized embryos at different times before the completion of the first cleavage, we found that the ability of dicoumarol to inhibit the first cell division was blocked if added after metaphase (90 minutes). See FIG. 5. These results suggest that coumarin compounds, such as dicoumarol, selectively inhibit cell cycle progression at prometaphase/metaphase of mitosis and any events prior to the beginning of M phase are not crucial to the activity of coumarin compounds.

Therefore, representative coumarin compounds, coumarin, 7-hydroxycoumarin, dicoumarol, esculetin and warfarin, were further studied for their effects on the polymerization of tubulin into microtubules in vitro and their effects on the growing and shortening dynamics of individual microtubules. The tubulin and microtubules were observed and evaluated by video microscopy, however, other methods known in the art may be used such as light scattering and sedimentation assays. These studies showed that coumarin compounds stimulate the polymerization of tubulin and microtubules in vitro.

For example, as shown in Table 1, about 0.1 $\mu$M dicoumarol affects the growing and shortening dynamics of eleven individual microtubules.

TABLE 1

Effects of Dicoumarol on the Dynamic Instability Parameters of Microtubule Plus Ends at Steady State

| | Concentration, $\mu$M | | | | | |
|---|---|---|---|---|---|---|
| | 0 | 0.04 | 0.1 | 1.0 | 10.0 | 50.0 |
| | Mean Rate ($\mu$m/min) | | | | | |
| Growing | 0.79 ± 0.10 | 0.61 ± 0.07 | 0.53 ± 0.10 | 0.63 ± 0.08 | 0.63 ± 0.10 | 0.54 ± 0.07 |
| Shortening | 18.50 ± 7.20 | 18.90 ± 8.10 | 12.10 ± 4.60 | 7.80 ± 4.80 | 7.40 ± 2.40 | 1.10 ± 0.20 |
| | Mean Length ($\mu$m/event) | | | | | |
| Growing | 0.86 ± 0.15 | 0.70 ± 0.09 | 0.61 ± 0.10 | 0.95 ± 0.22 | 0.58 ± 0.09 | 1.00 ± 0.17 |
| Shortening | 2.30 ± 0.58 | 2.00 ± 0.53 | 1.90 ± 0.43 | 1.40 ± 0.44 | 1.60 ± 0.37 | 1.40 ± 0.21 |
| | Mean Duration (min) | | | | | |
| Growing | 1.70 ± 0.52 | 1.30 ± 0.18 | 1.50 ± 0.29 | 1.70 ± 0.30 | 1.70 ± 0.38 | 2.36 ± 0.34 |
| Shortening | 0.53 ± 0.18 | 0.37 ± 0.13 | 1.10 ± 0.43 | 0.86 ± 0.34 | 0.51 ± 0.15 | 1.40 ± 0.07 |
| | Total Time (%) | | | | | |
| Growing | 59.4 | 60.3 | 34.7 | 32.3 | 20.7 | 41.9 |
| Shortening | 27.0 | 22.0 | 27.8 | 17.3 | 8.1 | 6.8 |
| Attenuated | 13.7 | 17.7 | 37.6 | 50.5 | 71.2 | 51.3 |
| | Transition Frequencies (events/min) | | | | | |
| Catastrophe | 0.62 | 0.70 | 0.22 | 0.24 | 0.11 | 0.07 |
| Rescue | 0.79 | 2.00 | 0.38 | 1.03 | 1.20 | 0.80 |
| Dynamicity | 1.50 | 1.20 | 0.65 | 0.43 | 0.24 | 0.31 |

±, standard error of the mean

Figure 6:
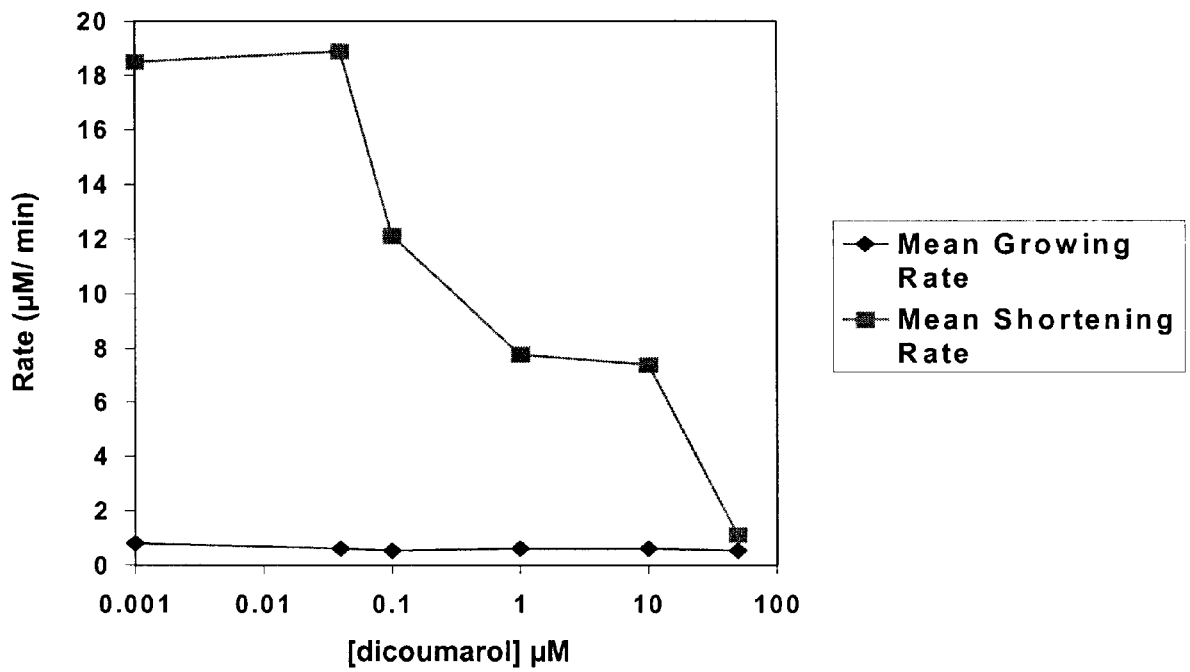
FIG. 6 shows the effect of different dicoumarol concentrations on mean growing and shortening rates.

Specifically, at 1 $\mu$M dicoumarol the mean shortening rate was significantly reduced by about 58%, from about 18.5 $\mu$M per minute to about 7.8 $\mu$m per minute, and reduced the lengths of a shortening excursion by about 40% from about 2.3 $\mu$m to about 1.4 $\mu$m. See FIG. 6. Previous results indicated that the mean shortening rate was reduced by about 72%, from about 18.5 $\mu$m per minute to about 5.2 $\mu$m per minute, and reduced the lengths of a shortening excursion by about 30% from about 2.3 $\mu$m to about 1.6 $\mu$M. This strong inhibition of steady-state shortening rate demonstrates that coumarin compounds, such as dicoumarol, stabilize microtubules by inhibiting the shortening rate. The shortening rate may be inhibited by strengthening the lateral interactions between tubulin subunits and adjacent protofilaments by conformational changes induced by the coumarin compound binding the tubulin along the length of the microtubule or at the ends of the microtubule.

Figure 7:
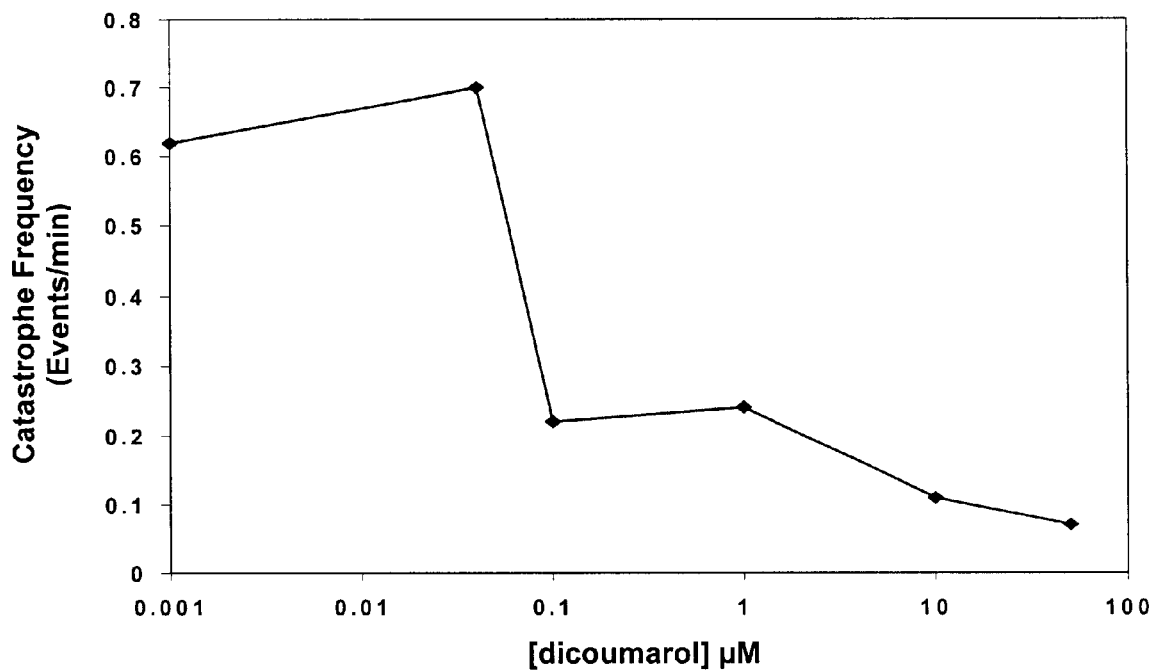
FIG. 7 illustrates the effect of various concentrations of dicoumarol on catastrophe frequency.

A microtubule comprises a labile tubulin-GDP core and a stable tubulin-GTP (or GDP-Pi) cap at the ends of the microtubule. Loss of the cap exposes the labile core and microtubule rapidly disassembles. The catastrophe and rescue frequencies are important parameters that reflect the loss or gain of the stabilizing GTP or GDP-Pi cap at microtubule ends. The transition from growing or attenuation to shortening is referred to as "catastrophe", and the transition from shortening to growing or attenuation is referred to as "rescue". See Walker et al. (1988) J. Cell Biol. 107:1437–1448, which is herein incorporated by reference. As shown in FIG. 7 dicoumarol decreased the frequency of catastrophe by about 65%, from about 0.62 μm to about 0.22 μm, at concentrations as low as about 0.1 μM, and increased the overall percentage of time in the paused (attenuated) state by about 63% at a concentration of about 0.1 μM. The pauses are periods during which growth or shortening at microtubule ends was not detectable.

Previous experiments showed that dicoumarol decreased the frequency of catastrophe by about 50%, from about 62 μm to about 0.31 μm, at concentrations as low as about 0.1 μM, and increased the overall percentage of time in the attenuated state by about 64% at a concentration of about 0.1 μM. Previous experiments also showed that dicoumarol decreased the frequency of catastrophe by about 72%, from about 0.75 μm to about 0.21 μm, and the rescue frequency by about 27% and increased the overall percentage of time in the paused (attenuated) state from about 33.8% to about 47.24%.

Catastrophe may occur upon loss of the last molecule of tubulin-GDP-Pi or tubulin-GTP and rescue may be initiated by binding of one or a few tubulin-GTP molecules in a favorable region at the end of a rapidly shortening microtubule. Dicoumarol may have reduced the catastrophe frequency either by lowering the rate of Pi release after GTP hydrolysis, by lowering the rate of during complex-GDP dissociation as compared to the dissociation rate for tubulin-GDP, or both. Such actions could be due to conformational changes induced in tubulin by binding of the coumarin compound. Thus, dicoumarol may be directly acting on stabilizing GTP or the GDP-Pi cap. Dicoumarol did not significantly alter the rescue frequency, thereby suggesting that dicoumarol does not directly affect the regain of a lost cap. This may be due to inhibition of GTP-tubulin addition by steric hindrance by the presence or binding of dicoumarol at the microtubule end, thereby preventing cap regain.

The strong effects on the catastrophe frequencies indicate that coumarin compounds, such as dicoumarol, act directly on the cap by reducing the rate of GTP hydrolysis or Pi release. Therefore, dicoumarol bound tubulin-GDP may dissociate more slowly than unliganded tubulin-GDP because of a conformational change induced in the tubulin by dicoumarol that mimics the conformation of the stabilizing tubulin-GTP cap. As taxol-like compounds do not directly alter the cap, coumarin compounds most likely stabilize microtubules in a manner different to taxol-like compounds. Therefore, a coumarin compound may be used in conjunction with taxol to provide a dual or synergistic effect.

Figure 8:
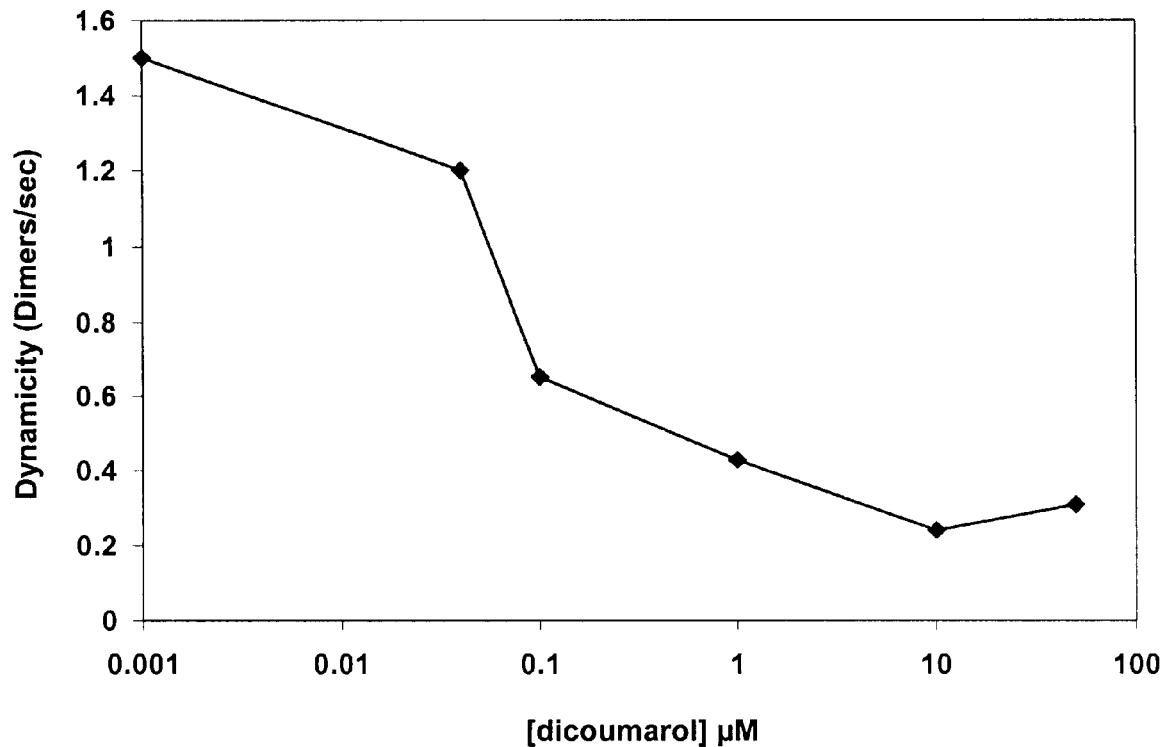
FIG. 8 shows the suppression of dynamicity of different concentrations of dicoumarol.

There was no significant change in the average rate or lengths of growth at various dicoumarol concentrations. Thus, dicoumarol strongly decreased the rates and lengths of microtubule shortening, while it unaffected the microtubule growing rate or lengths of growth. In addition, dynamicity was significantly reduced by about 57% (previous results indicated about 64%) at a dicoumarol concentration of about 0.1 μM. See FIG. 8. "Dynamicity" is the sum of the gain and loss (exchange) of tubulin subunits at the microtubule ends and is a measure of overall dynamic instability. Dynamicity is calculated from all detectable growing and shortening events including the time spent in attenuated state. See Toso et al. (1993) Biochem 32(5):1285–1293 and Panda et al. (1994) PNAS USA 91(24): 11358–11362, both of which are herein incorporated by reference. Thus, at 1 μM, rates and lengths of microtubule shortening events were inhibited, the percentage of time in pause was increased, and the overall dynamicity of the microtubule was inhibited. Dicoumarol significantly increased the percentage of time the microtubule spent in an attenuated state (pause) by about 64% (about 0.1 μM), significantly decreased the percentage of time spent in a shortening phase and decreased the percentage of time spent in a growing phase. Therefore, coumarin compounds, such as dicoumarol, suppress, prevent, inhibit, or modulate the growing and shortening dynamics of microtubules.

Figure 9:
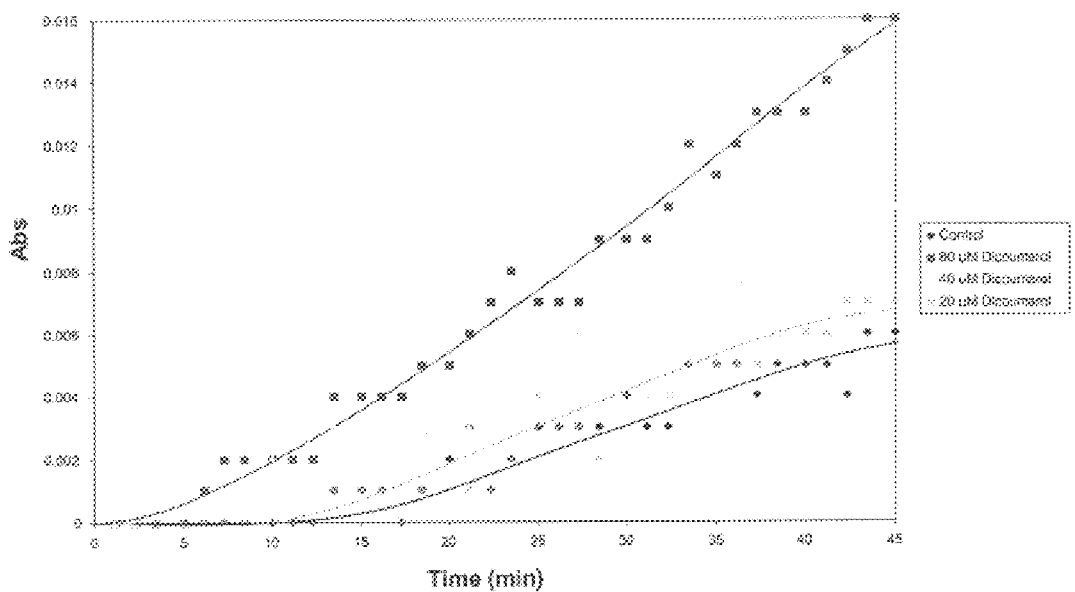
FIG. 9 shows the results of a light scattering assay of different concentrations of dicoumarol.

The effect of dicoumarol on microtubule assembly is shown in FIG. 9. In the presence of dicoumarol (0 μM-80 μM) there appeared to be a concentration-dependent increase in the rate and extent of polymerization of tubulin (12 μM). The increase in turbidity was gradual, and after 45 minutes of incubation steady state was not reached. Electron microscopy studies were conducted in order to examine the morphology of the polymers formed during the polymerization process at 10, 20, and 45 minutes in the presence of dicoumarol. No microtubules were formed in the dicoumarol containing samples after polymerization for a period of 10 and 20 minutes. Only extensive tubulin aggregates of various sizes could be visualized. However, microtubules were produced in the presence of 100 μM dicoumarol if polymerization was prolonged to 45 minutes. The electron microscopy studies were repeated with axoneme seeded microtubules and the results indicated that the potency in inducing microtubule assembly reactions was not significantly increased. However, electron micrograph views of the polymer formed with dicoumarol in the presence of axonemal seeded microtubules revealed actual microtubule structures at concentrations of 20 μM. These results demonstrate that dicoumarol weakly induces polymerization microtubules in the presence or absence of a microtubule nucleating structure.

Figure 10:
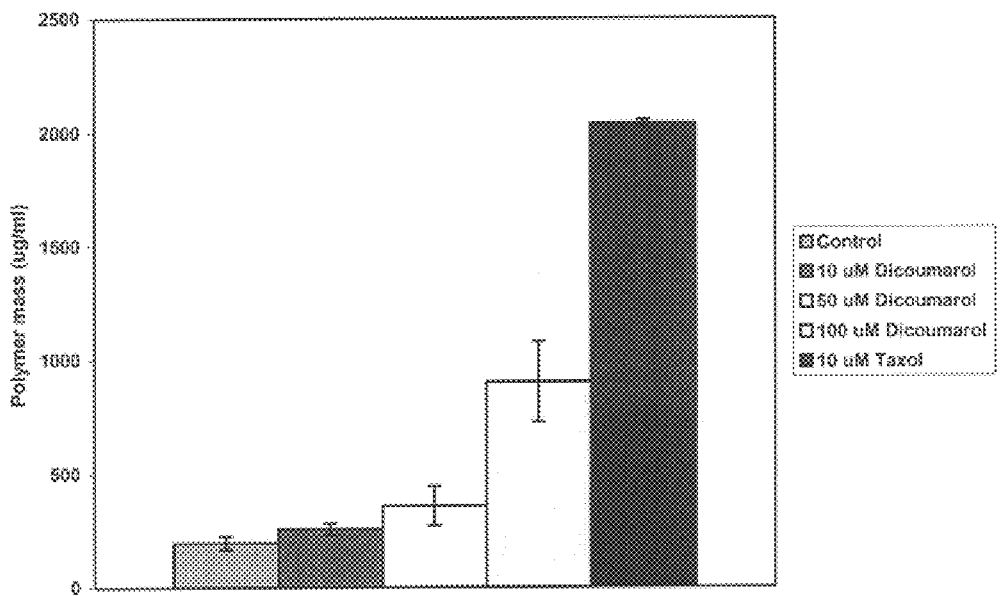
FIG. 10 shows the effects of different concentrations of dicoumarol on the steady state microtubule mass.

The induction of tubulin assembly by dicoumarol was further examined by a sedimentation assay of axoneme seeded microtubules at varying dicoumarol concentrations. See FIG. 10. Polymerization of microtubules in the presence of low concentrations of dicoumarol (less than about 10 μM) had no significant effect on the mass of polymer formed as compared with controls. At 50 μM dicoumarol, the polymer mass was increased by about 16%. Significant induction of polymerization occurred at dicoumarol concentration above 100 μM. Similar results were obtained when microtubules were polymerized in the presence "axonemal seeds".

Specifically, by using a polymer mass assay, purified bovine brain tubulin was assembled to polymer mass steady state at 37° C. in the presence of dicoumarol. "Steady state" is the concentration of tubulin in equilibrium with assembled microtubules. Pure tubulin will polymerize into microtubules at 37° C. in a test tube so long as magnesium and GTP are present. Polymerization continues until it reaches a critical concentration (steady state) where the final concentration of free tubulin at the plateau where the polymerization and depolymerization rates are balanced. The microtubules were then separated from unpolymerized tubulin by sedimentation and the protein concentration of the supernatant (free tubulin) was determined by the Bradford method (Bradford, M. M. (1976) Anal. Biochem. 72:248–354, which is herein incorporated by reference).

Interestingly, the ability of dicoumarol to stimulate microtubule polymerization is relatively weak compared with its ability to stabilize microtubule dynamics. Turbidity and sedimentation assays of dicoumarol showed minimal effect on polymer mass. Electron micrographs revealed that in the absence of axonemes, tubulin aggregates were formed and very few actual microtubule structures were seen at high dicoumarol concentrations (100 $\mu$M). These data suggests that dicoumarol is weakly effective in promoting (hypernucleating) tubulin assembly, but does potently stabilize microtubule dynamics and thus prevents polymer disassembly. If dicoumarol suppresses microtubule dynamics in cells as it does in vitro, this kinetic stabilization may prevent spindle microtubules from reaching the kinetechores and aligning them at the metaphase plate.

In pursuing the nature of this inhibition of microtubule dynamics, the effects of dicoumarol on microtubule morphology in cells were examined. Microtubule dynamics increase 20- to 100-fold as a cell transitions from interphase to mitosis. See Saxton et al. (1984) J. Cell Biol. 99(6): 2175–2186, which is herein incorporated by reference. In prometaphase of mitosis, microtubules nucleating from the spindle poles undergo phases of growth and shortening in order probe the cytoplasm of the cell and establish contacts with the kinetechores of a chromosome. See Hayden et al. (1990) J. Cell Biol. 111(3):1039–1045, which is herein incorporated by reference. It is believed that progression of metaphase to anaphase requires ample tension or the attachment of an appropriate number of microtubules to kinetochores and any kinetochore that is not attached to microtubules generates a diffusible signal that prevents completion of mitosis before progression into anaphase is allowed. If dicoumarol suppresses microtubule dynamics in cells as it does in vitro, this kinetic stabilization may prevent spindle microtubules from reaching the kinetechores and aligning them at the metaphase plate. Examination of microtubule and chromosome organization by FITC-conjugated tubulin antibody and DAPI staining showed that the chromosomes and spindle microtubules of dicoumarol treated embryos were significantly altered. The microtubules in these cells were much longer relative to the control. In addition, the chromosomes had not congressed to the metaphase plate and appeared to remain in an intact nuclear envelope.

Figure 11:
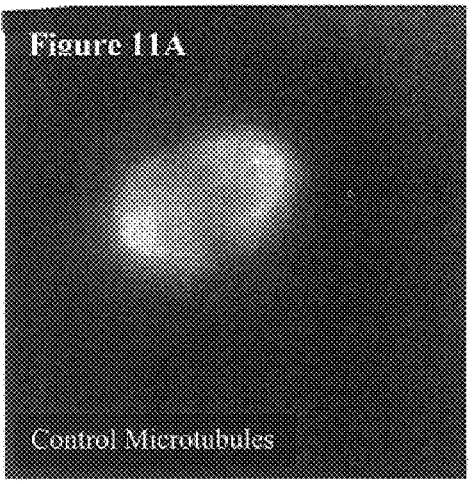
FIG. 11A shows microtubules in mitotic HeLa control cells.
FIG. 11B shows chromosomes in mitotic HeLa control cells.
FIG. 11C shows microtubules in mitotic HeLa cells treated with 50 $\mu$M dicoumarol.
FIG. 11D shows chromosomes in mitotic HeLa cells treated with 50 $\mu$M dicoumarol.
Figure 11:
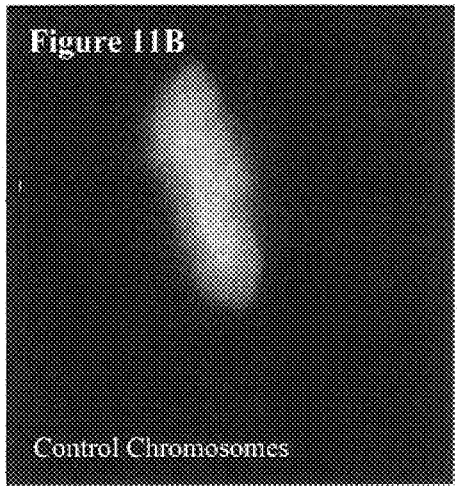
Figure 11:
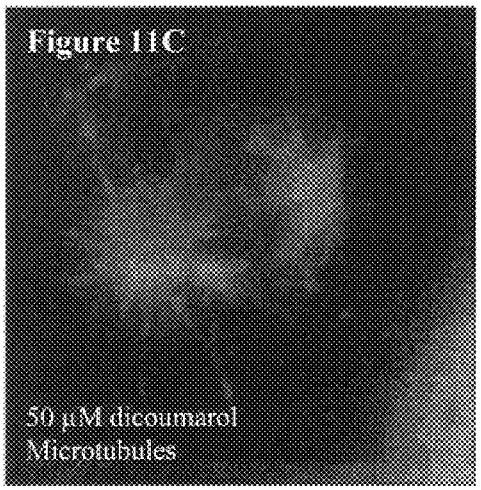
Figure 11:
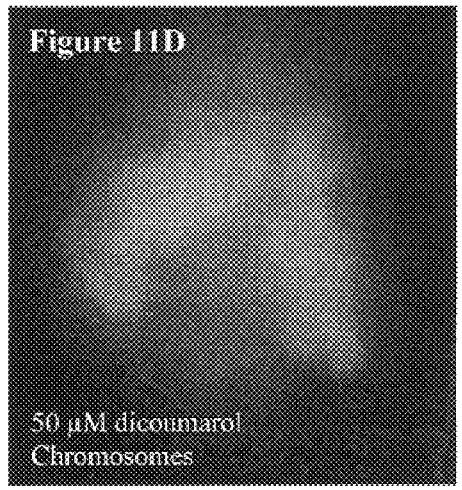

The coumarin compounds were also found to effect mitotic spindle organization. Specifically, HeLa cells incubated for about 20 hours with a range of dicoumarol concentrations blocked mitosis at the transition form metaphase to anaphase in the HeLa cells. The cells were then fixed and processed for fluorescence microscopy to determine the arrangement of chromatin or chromosomes using 4,6-diamidino-2-phenylindole (DAPI, a nuclear, DNA stain) and the microtubules using anti-tubulin immunofluorescence. Indirect immunofluorescence staining of microtubules and 4,6-diamidino-2-phenylindole staining of chromatin were used to characterize the effects of the coumarin compounds on the distribution of the cells in stages of the cell cycle and on the organization of microtubules and chromosomes in metaphase spindles. Examination of microtubule organization by FITC-conjugated tubulin antibody staining showed that at low concentrations, dicoumarol did not produce discernible changes in the organization of interphase cytoplasmic microtubules. At high concentrations, about 10 $\mu$M, dicoumarol produced abnormal organization of mitotic spindle microtubules in HeLa cells. See FIG. 11C. In control cells, the metaphase spindles were bipolar and contained a compact equatorial plate of condensed chromosomes. See FIGS. 11A and 11B. At about 10 $\mu$M of dicoumarol, the organization of many spindles was abnormal, e.g., the spindles were tripolar or multipolar and contained chromosomes that had not congressed to the metaphase plate and were located near the spindle poles. See FIG. 11D. Failure to congress to the metaphase plate may be due to the inability of the microtubules to capture the kinetochores or to elongate properly during congression.

From these studies, a notable difference between the action of coumarin compounds, such as dicoumarol, on microtubules as compared with the actions of vinblastine and taxol was observed. Unlike vinblastine and taxol, high concentrations of dicoumarol does not induce microtubule bundling or tubulin paracrystal formation which suggests that coumarin compounds, such as dicoumarol, affects or interacts with microtubules in a manner distinct from vinblastine and taxol.

The binding of dicoumarol was determined by taking advantage of the fluorescence properties of tubulin. Tubulin is a tryptophan containing protein. When excited, tubulin displays a typical tryptophan emission spectrum. An excitation wavelength was selected to specifically excite the tubulin tryptopanyl residues. Relative fluorescence intensities were measured and buffer blanks were subtracted from all measurements. By incubating tubulin with different concentrations of dicoumarol, whether there is concentration dependence between the binding of dicoumarol and the quenching of tubulin fluorescence was determined. See Panda et al. (1992) Eur. J. Biochem. 204:783–787; Panda et al. (1997) PNAS USA 94:10560–10564; and Panda et al (1997) J. Biol. Chem. 272:7681–7687, which are herein incorporated by reference.

Figure 12:
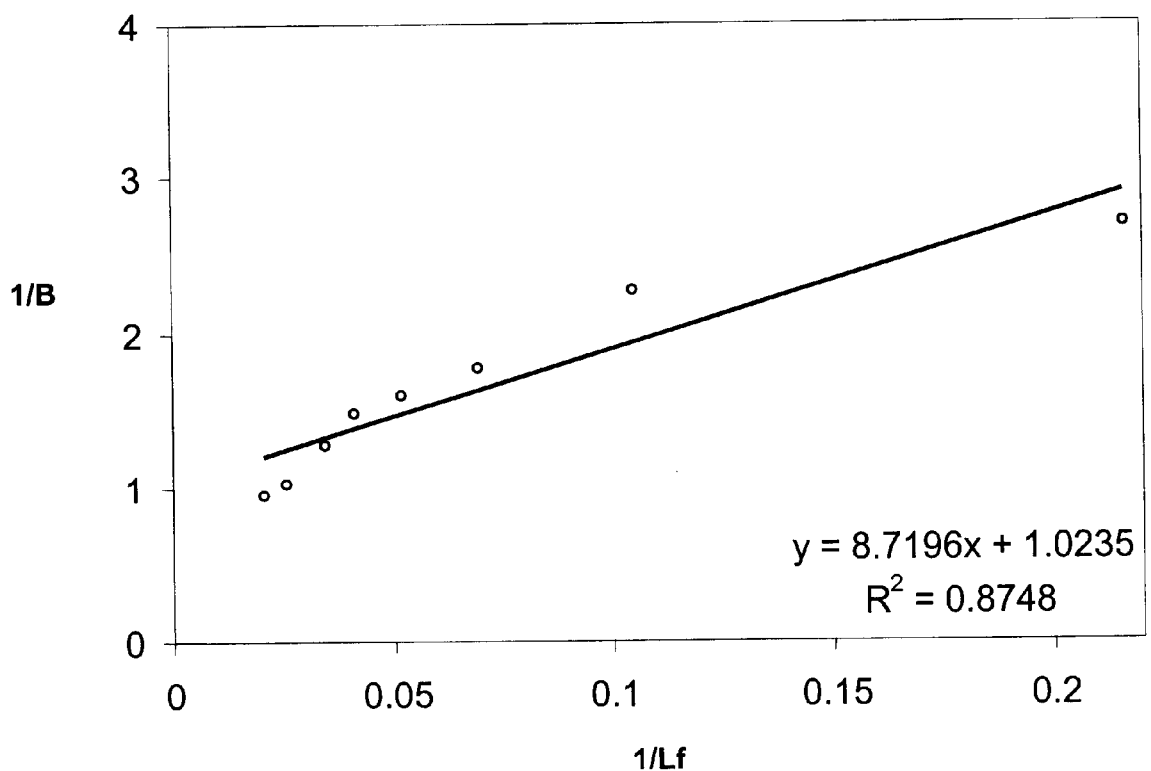
FIG. 12 is a graph providing the binding constant of dicoumarol to tubulin.
Figure 13A:
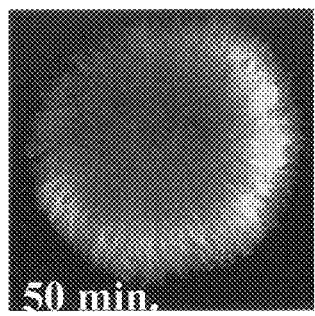
FIG. 13 shows microtubules in sea urchin embryo control cells at 50, 70, 80, 90, 100, and 110 minutes.
Figure 13B:
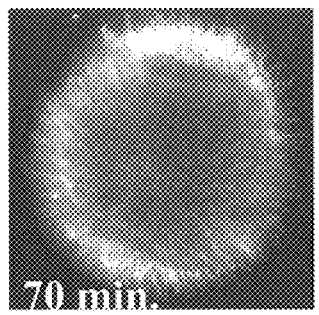
Figure 13C:
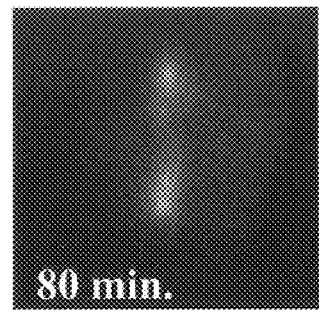
Figure 13D:
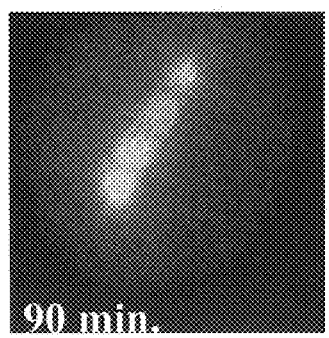
Figure 13E:
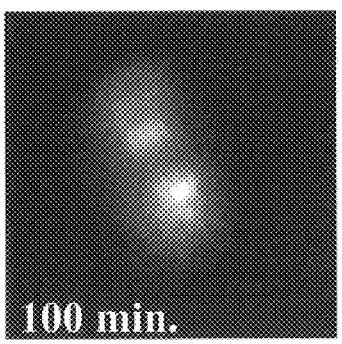
Figure 13F:
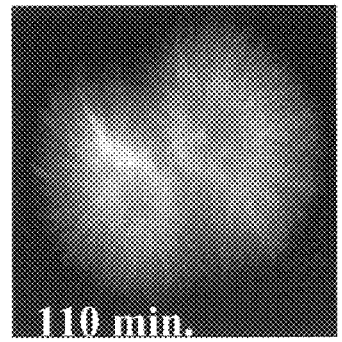

As explained in detail in Example 5 below, the binding of dicoumarol and the quenching of tubulin fluorescence were determined to be concentration dependent. The data were analyzed and plotted as 1/alpha versus 1/free drug, wherein alpha=the fractional occupancy of the binding site, to give a slope that provides the dissociation constant, $K_d$, of dicoumarol as 8.72 $\mu$M. See FIG. 12.

As described herein, the coumarin compounds represent a new structurally distinct class of compounds that stabilize tubulin polymer and enhance microtubule assembly reactions. The coumarins are not similar to taxol-like compounds in inducing tubulin polymerization into microtubules in vitro. As explained herein, similar to taxol-like compounds, coumarin compounds stabilize microtubules, however, the stabilization may occur in a manner different from the taxanes. As disclosed herein, coumarin compounds suppress, inhibit, prevent or modulate microtubule dynamics in a manner that affects the ability of a cell, such as a cancer cell, to properly assemble a mitotic spindle, to pass the metaphase/anaphase checkpoint and produce progeny cells. As the inhibition of microtubule growing and shortening dynamics by coumarin compounds may lead to the inability of some chromosomes to congress to the metaphase plate because the microtubules emanating from both spindle poles are prevented from reaching the kinetochores, coumarin compounds may be used to treat, prevent, or inhibit diseases and disorders related to microtubule formation, function, or both.

Thus, the present invention provides coumarin compounds having the basic structural formula

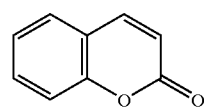

for a core or backbone structure, wherein the benzene ring, the pyrone or both may comprise at least one substituent in methods for treating diseases and disorders associated with microtubule formation and function. Preferred coumarin compounds include coumarin, dicoumarol, umbelliferone, esculetin, warfarin, 7-hydroxycoumarin, 3,6,7-trihydroxycoumarin, and derivatives thereof As used herein, coumarin compound "derivatives" include compounds that comprise the coumarin backbone, a benzo-α-pyrone.

The terms and abbreviations used in the instant disclosure have their normal meanings unless otherwise designated. Several terms employed throughout the present application are described below.

In accordance with a convention used in the art,

is used in structural formulas herein to depict the bond that is the point of attachment of the moiety or substituent to the core or backbone structure.

Where chiral carbons are included in chemical structures, unless a particular orientation is depicted, both sterioisomeric forms are intended to be encompassed.

An "alkyl group" is intended to mean a straight or branched chain monovalent radical of saturated and/or unsaturated carbon atoms and hydrogen atoms, such as methyl (Me), ethyl (Et), propyl (Pr), isopropyl (i-Pr), butyl (Bu), isobutyl (i-Bu), t-butyl (t-Bu), ethenyl, pentenyl, butenyl, propenyl, ethynyl, butynyl, propynyl, pentynyl, hexynyl, and the like, which may be unsubstituted (i.e., contain only carbon and hydrogen) or substituted by one or more suitable sustituents as defined below (e.g., one or more halogen, such as F, Cl, Br, or I, with F and Cl being preferred). A "lower alkyl group" is intended to mean an alkyl group having from 1 to 8 carbon atoms in its chain.

A "cycloalkyl group" is intended to mean a non-aromatic monovalent monocyclic, bicyclic, or tricyclic radical comprising 3–14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more substituents. Illustrative examples of cycloalkyl groups include the following moieties:

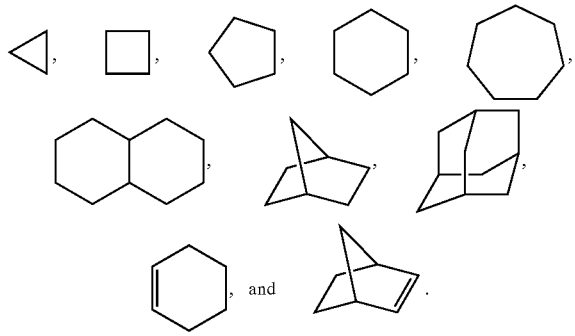

A "heterocycloalky group" is intended to mean a non-aromatic monovalent monocyclic, bicyclic, or tricyclic radical, which is saturated or unsaturated, comprising 3–18 ring members, which includes 1–5 heteroatoms selected from nitrogen, oxygen, and sulfur, where the radical is unsubstituted or substituted by one or more suitable sub-stituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include the following moieties:

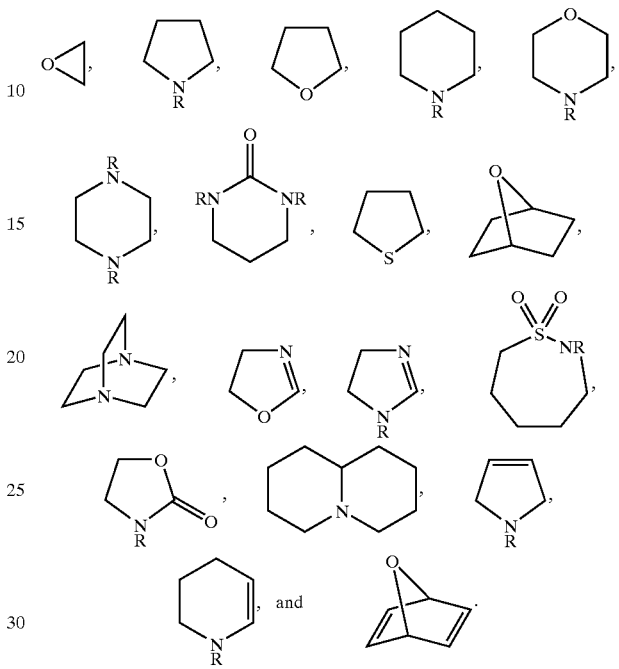

An "aryl group" is intended to mean an aromatic monovalent monocyclic, bicyclic, or tricyclic radical comprising 6, 10, 14, or 18 carbon ring members, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl). Illustrative examples of aryl groups include the following moieties:

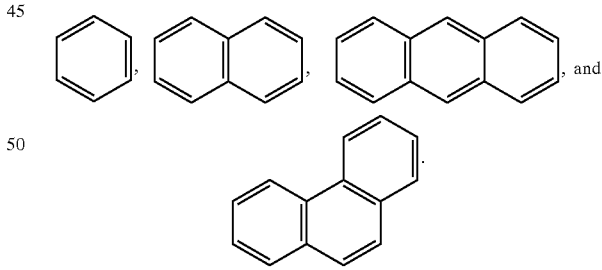

A "heteroaryl group" is intended to mean an aromatic monovalent monocyclic, bicyclic, or tricyclic radical comprising 4–18 ring members, including 1–5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include the following moieties:

A "heterocycle" is intended to mean a heteroaryl or heterocycloalkyl group (each of which, as defined above, are optionally substituted).

The terms "aryl" (Ar) and "heteroaryl" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like.

An "acyl group" is intended to mean a —C(O)—$R_a$ radical, where $R_a$ is a suitable substituent as defined below.

A "thioacyl group" is intended to mean a —C(S)—$R_a$ radical, where $R_a$ is a suitable substituent as defined below.

A "sulfonyl group" is intended to mean a —$SO_2R_a$ radical, where $R_a$ is a suitable substituent as defined below.

A "hydroxyl group" is intended to mean the radical —OH.

An "amino group" is intended to mean the radical —$NH_2$.

An "alkylamino group" is intended to mean the radical —$NHR_a$, where $R_a$ is an alkyl group.

A "dialkylamino group" is intended to mean the radical —$NR_aR_b$, where $R_a$ and $R_b$ are each independently an alkyl group.

An "alkoxyl group" is intended to mean the radical —$OR_a$, where $R_a$ is an alkyl group. Exemplary alkoxyl groups include methoxyl, ethoxyl, propoxyl, and the like.

An "alkoxycarbonyl group" is intended to mean the radical —C(O)$OR_a$, where $R_a$ is an alkyl group.

An "alkylsulfonyl group" is intended to mean the radical —$SO_2R_a$, where $R_a$ is an alkyl group.

An "alkylaminocarbonyl group" is intended to mean the radical —C(O)$NHR_a$, where $R_a$ is an alkyl group.

A "dialkylaminocarbonyl group" is intended to mean the radical —C(O)$NR_aR_b$, where $R_a$ and $R_b$ are each independently an alkyl group.

A "mercapto group" is intended to mean the radical —SH.

An "alkylthio group" is intended to mean the radical —$SR_a$, where $R_a$ is an alkyl group.

A "carboxyl group" is intended to mean the radical —C(O)OH.

A "carbamoyl group" is intended to mean the radical —C(O)$NH_2$.

An "aryloxyl group" is intended to mean the radical —$OR_c$, where $R_d$ is an aryl group.

A "heteroaryloxyl group" is intended to mean the radical —$OR_d$, where $R_d$ is a heteroaryl group.

An "arylthio group" is intended to mean the radical —$SR_c$, where $R_c$ is an aryl group.

A "heteroarylthio group" is intended to mean the radical —$SR_d$, where $R_d$ is a heteroaryl group.

A "leaving group" (Lv) is intended to mean any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

A "protecting group" is intended to refer to groups that protect one or more inherent functional group from premature reaction. Suitable protecting groups may be routinely selected by those skilled in the art in light of the functionality and particular chemistry used to construct the compound. Examples of suitable protecting groups are described, for example, in Greene and Wutz, PROTECTING GROUPS IN ORGANIC SYNTHESIS, $2^{nd}$ edition, John Wiley and Sons, New York, N.Y. (1991).

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxy groups, carboxyl groups, amino groups, alkylamino groups, dialkylamino groups, carbamoyl groups, arylthio groups, heteroarylthio groups, and the like.

In general, the various moieties or functional groups for variables in the formulae may be "optionally substituted" by one or more suitable "substituents". The term "substituent" or "suitable substituent" is intended to mean any suitable substituent that may be recognized or selected, such as through routine testing, by those skilled in the art. Illustrative examples of useful substituents are those found in the exemplary compounds that follow, as well as halogen (chloro, iodo, bromo, or fluoro); $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano; amido; phosphonato; phosphine; carboxyl; carbonyl; aminocarbonyl; thiocarbonyl; sulfonyl;

sulfonamine; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O. All of these substituents may optionally be further substituted with a substituent selected from groups such as hydroxyl groups, halogens, oxo groups, alkyl groups, acyl groups, sulfonyl groups, mercapto groups, alkylthio groups, alkyloxyl groups, cycloalkyl groups, heterocycloalkyl groups, aryl groups, heteroaryl groups, carboxyl groups, amino groups, alkylamino groups, dialkylamino groups, carbamoyl groups, aryloxyl groups, heteroaryloxyl groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

It is understood that while a coumarin compound of the general structural formulas herein may exhibit the phenomenon of tautomerism, the structural formulas within this specification expressly depict only one of the possible tautomeric forms. It is therefore to be understood that the structural formulas herein are intended to represent any tautomeric form of the depicted compound and is not to be limited merely to a specific compound form depicted by the structural formulas.

It is also understood that the structural formulas are intended to represent any configurational form of the depicted compound and is not to be limited merely to a specific compound form depicted by the structural formulas.

Some of the coumarin compounds may exist as single stereoisomers (i.e., essentially free of other stereoisomers), racemates, or mixtures of enantiomers, diastereomers, or both. All such single stereoisomers, racemates and mixtures thereof are intended to be within the scope of the present invention. Preferably, the coumarin compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, if the compounds of the present invention are made synthetically, they are used in a form that is at least 90% optically pure, that is, a form that comprises at least 90% of a single isomer (80% enantiomeric excess (e.e.) or diastereomeric excess (d.e.), more preferably at least 95% (90% e.e. or d.e.), even more preferably at least 97.5% (95% e.e. or d.e.), and most preferably at least 99% (98% e.e. or d.e.).

Additionally, the structural formulas herein are intended to cover, where applicable, solvated as well as unsolvated forms of the coumarin compounds. A "solvate" is intended to mean a pharmaceutically acceptable solvate form of a specified compound that retains the biological effectiveness of such compound. Examples of solvates include a coumarin compound in combination with water, isopropanol, ethanol, methanol, dimethyl sulfoxide, ethyl acetate, acetic acid, ethanolamine, or acetone. Also included are miscible formulations of solvate mixtures such as a compound of the invention in combination with an acetone and ethanol mixture. Thus, the structural formulas include compounds having the indicated structure, including the hydrated as well as the non-hydrated forms.

As indicated above, the compounds of the invention also include active tautomeric and stereoisomeric forms of coumarin compounds, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

Pharmaceutical compositions according to the invention may, alternatively or in addition to a given coumarin compound, comprise as an active ingredient a pharmaceutically acceptable salt, prodrug, or active metabolite thereof. Such compounds, salts, prodrugs, and metabolites are sometimes referred to herein collectively as "microtubule stabilizing agents". Such non-peptide agents are often pharmaceutically advantageous over peptide agents since they provide better biodistribution and tolerance to degradation by physiological enzymes.

A "pharmaceutically acceptable salt" is intended to mean a salt that retains at least the substantial biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

If the coumarin compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrovic acid, oxalic acid, glycolic acid, salicylic acid, a pyranosidyl acid, such as glucuronic acid or galacturonic acid, an alpha-hydrozy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the coumarin compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of stabilizing agents that are solids, it is understood by those skilled in the art that the coumarin compounds and salts may exist in different crystal or polymorphic forms, all of which are intended to be within the scope of the present invention.

The affinity of a coumarin compound for a target, such as a microtubule or receptor, may be enhanced by providing multiple copies of the ligand in close proximity, preferably using a scaffolding provided by a carrier moiety. Such multivalent or multimeric forms of active forms of the coumarin compounds are referred to herein as "multimers". Multimers of various dimensions, i.e., bearing varying numbers of copies of a coumarin compound, may be tested to arrive at a multimer of optimum size with respect to interaction with or binding to the target. Provision of such multivalent forms of active receptor-binding compounds with optimal spacing between the receptor-binding moieties may enhance receptor binding. See e.g., Lee et al. (1984) Biochem. 23:4255. The artisan may control the multivalency and spacing by selection of a suitable carrier moiety or linker units. Useful moieties include molecular supports containing a multiplicity of functional groups that can be reacted with functional groups associated with the active compounds of the invention. A variety of carrier moieties may be used to build highly active multimers, including proteins such as BSA (bovine serum albumin) or HAS, peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

"A pharmaceutically acceptable prodrug" is a compound that may be converted under physiological conditions or by solvolysis to the specified compound or to a pharmaceutically acceptable salt of such compound.

"A pharmaceutically active metabolite" is intended to mean a pharmacologically active product produced through metabolism in the body of a specified compound or salt thereof.

Prodrugs and active metabolites of a compound may be identified using routine techniques known in the art. See e.g., Bertolini, G. et al. (1997) J. Med. Chem., 40:2011–2016; Shan, D. et al. J. Pharm. Sci., 86(7): 765–767; Bagshawe K. (1995) Drug Dev. Res., 34:220–230; Bodor, N. (1984) Advances in Drug Res., 13:224–331; Bundgaard, H., DESIGN OF PRODRUGS (Elsevier Press 1985); and Larsen, I or II. K., DESIGN AND APPLICATION OF PRODRUGS, DRUG DESIGN AND DEVELOPMENT. Krogsgaard-Larsen et al., eds., Harwood Academic Publishers (1991).

Coumarin compounds and compositions that inhibit, prevent, regulate, modulate, attenuate, stabilize, or affect microtubule formation or function are desirable and are one preferred embodiment of the present invention. The present invention is further directed to methods of inhibiting, preventing, regulating, modulating, attenuating, stabilizing, or affecting microtubule formation or function, by administering the microtubule stabilizing agent of the present invention.

The microtubule stabilizing agents in accordance with the present invention are useful for treating diseases and disorders associated with microtubule formation or function in a subject. Preferably the subject is mammalian, more preferably human. The diseases and disorders associated with microtubule formation or function include cancer, fungal diseases such as candida and aspergillus, cysts, Alzheimer's disease, gout, malaria, atherosclerosis, restenosis, chronic inflammation, rheumatoid arthritis, psoriasis, diabetic retinopathy, chronic obstructive pulmonary disorder, tuberculosis, chronic cholecystitis, osteoarthritis, rheumatic carditis, bronchiectasis, Hashimoto's thyroiditis, and the like.

The activity of a coumarin compound as a microtubule stabilizing agent, may be measured by any of the methods available to those skilled in the art, including in vivo and/or in vitro assays such as those set out in the examples below.

The microtubule stabilizing agents in accordance with the present invention may be used in combination with a supplementary active compound or as a substitution for treating a subject suffering from a disease or disorder associated with microtubule formation or function. For example, a coumarin compound may be used alone or combination with a supplementary active compound such as an anti-neoplastic agent to treat cancer or an antimalarial to treat malaria. A coumarin compound of the invention may be used alone or in combination with another microtubule stabilizing agent, such as taxol, or a second coumarin compound to treat, prevent or inhibit Alzheimer's disease. For methods of treating Alzheimer's disease with taxol, see U.S. Pat. No. 5,580,898, which is herein incorporated by reference. Other supplementary compounds include alkoids, vistbine, estramustine, amphotericin B and griseofulvin for treating a variety of cancers, fungal diseases and parasitic infections.

A particular coumarin compound, a particular supplementary compound, or both may be chosen to selectively treat a given disease or disorder. For example, a particular coumarin compound, such as 3,6,7-trihydroxy coumarin, may have a greater affinity for microtubules in fungal cells than mammalian, preferably human, cells. Therefore, 3,6,7-trihydroxy coumarin would be the preferred coumarin compound to treat a fungal disease. If combination therapy for treating the fungal disease is desired, a supplementary compound which is an anti-fungal, such as griseofulvin, would be preferred. For treating a cancer patient, a coumarin compound that does not exhibit anti-coagulant properties, such as 7-hydroxycoumarin, would be preferred as chemotherapy often makes the patient more susceptible to bleeding.

A microtubule stabilizing agent of the present invention may be administered in a therapeutically effective amount to a mammal such as a human. Therapeutically effective amounts of the microtubule stabilizing agents of the invention may be used to inhibit, prevent, regulate, modulate, attenuate, stabilize, or affect microtubule formation or function. An "effective amount" is intended to mean that amount of an agent that, when administered to a cell or organism, is sufficient to inhibit, prevent, regulate, modulate, attenuate, stabilize, or affect microtubule formation or function. For example, a therapeutically effective amount of a coumarin compound, or salt, prodrug, or active metabolite thereof or salt of such metabolite, is a quantity sufficient to inhibit, prevent, regulate, modulate, attenuate, stabilize, or affect microtubule formation or function in the cell or organism. The amount of a given agent that will correspond to such an amount will vary depending upon factors such as the particular coumarin compound, the given drug or compound, the pharmaceutical formulation and route of administration, and the identity of the subject or host being treated, but can nevertheless be routinely determined by one skilled in the art.

For example, a therapeutically effective amount of a compound of the invention ranges from about 0.01 to about 5,000 mg/kg body weight, preferably about 0.1 to about 2,500 mg/kg body weight, and more preferably about 1 to about 1,000 mg/kg body weight. Preferred topical concentrations include about 0.1% to about 15%, more preferably about 5% to about 10%, in a formulated salve.

The skilled artisan will appreciate that certain factors may influence the dosage required to effectively treat a subject, including but not limited to the severity of the disease or disorder, previous treatments, the general health and/or age of the subject, and other diseases present.

Moreover, treatment of a subject with a therapeutically effective amount of the microtubule stabilizing agent can include a single treatment or, preferably, can include a series of treatments.

In a preferred example, a subject is treated with an amount of a coumarin compound ranging between about 0.1 to about 5,000 mg/kg body weight, at least one time per week for between about 1 to about 10 weeks, and preferably between about 2 to about 8 weeks, and more preferably between about 4 to about 6 weeks. In some conditions chronic administration may be required.

It will also be appreciated that the effective dosage of the compound used for treatment may increase or decrease over the course of a particular treatment. Changes in dosage may result and become apparent by standard diagnostic assays known in the art. For example, a solution of about 10 mg of a coumarin compound prepared in about 10 ml of saline may be administered i.v. to a subject in a single daily dose of about 0.1 mg/kg to about 0.15 mg/kg. The hematological responses, such as leukopenia, are observed over a period of about 7 to about 10 days wherein the dosages are adjusted accordingly. The daily dose may increase gradually, about 0.05 mg/kg, until toxicity is observed.

The pharmaceutical compositions of the invention may be prepared in a unit-dosage form appropriate for the desired mode of administration. The compositions of the present invention may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the condition to be treated, and the chosen active compound.

It will be appreciated that the actual dosages of the agents used in the compositions of this invention will vary according to the particular complex being used, the particular composition formulated, the mode of administration, and the particular site, host, and disease being treated. Optimal dosages for a given set of conditions may be ascertained by those skilled in the art using conventional dosage-determination tests in view of the experimental data for a given coumarin compound. Dosages of prodrugs may be at weight levels that are chemically equivalent to the weight levels of the fully active forms.

The inventive agents may be formulated into pharmaceutical compositions as described below. Pharmaceutical compositions of this invention comprise an effective amount of a coumarin compound and an inert, pharmaceutically acceptable carrier or diluent. In one embodiment of the pharmaceutical compositions, efficacious levels of the microtubule stabilizing agents are provided so as to provide therapeutic benefits involving inhibiting, preventing, regulating, modulating, attenuating, stabilizing, or affecting microtubule formation or function. By "efficacious levels" is meant levels in which a cell's or organism's polymerized tubulin or microtubule mass is increased or stabilized as compared to a control. These compositions are prepared in unit-dosage form appropriate for the mode of administration, e.g., parenteral or oral administration.

The microtubule stabilizing agents may be administered by any of a variety of suitable routes, such as orally, rectally, transdermally, subcutaneously, intravenously, intramuscularly, or intranasally. The agents are preferably formulated into compositions suitable for the desired routes before being administered. Such formulations are well known in the art. See e.g. REMINGTON: THE SCIENCE AND PRACTICE OF PHARMACY, $20^{th}$ ed. Lippincott Williams & Wilkins, Baltimore, Md. (2000).

Microtubule stabilizing agent is preferably administered in conventional dosage form prepared by combining a therapeutically effective amount of at least one of the microtubule stabilizing agents of the invention as an active ingredient with appropriate pharmaceutical carriers or diluents according to conventional procedures. These procedures may involve mixing, granulating and compressing or dissolving the ingredients as appropriate to the desired preparation.

A pharmaceutical composition or preparation according to the invention comprises an effective amount of at least one active ingredient including at least one microtubule stabilizing agent of the invention and a pharmaceutically acceptable carrier, such as a diluent or excipient for the agent. Other active ingredients include drugs and compounds used for treating, preventing or inhibiting a given disease or disorder. Active ingredients also include the drugs or compounds to which the microtubule stabilizing agent inhibits, prevents, regulates, modulates, attenuates, stabilizes, or affects microtubule formation or function. For example, a pharmaceutical composition of the present invention may include at least one microtubule stabilizing agent as disclosed herein and taxol as active ingredients to treat, prevent, or inhibit cancer in a subject who may not be responding to taxol therapy well.

When the carrier serves as a diluent, it may be a solid, semi-solid, or liquid material acting as a vehicle, excipient, or medium for the active ingredient. Compositions according to the invention may be made by admixing the active ingredient with a carrier, or diluting it with a carrier, or enclosing or encapsulating it within a carrier, which may be in the form of a capsule, sachet, paper container, or the like. Exemplary ingredients, in addition to one or more cell-cycle control agents and any other active ingredients, include Avicel (microcrystalline cellulose), starch, lactose, calcium sulfate dihydrate, terra alba, sucrose, talc, gelatin, agar, pectin, acacia, magnesium stearate, stearic acid, peanut oil, olive oil, glyceryl monostearate, Tween 80 (polysorbate 80), 1,3-butanediol, cocoa butter, beeswax, polyethylene glycol, propylene glycol, sorbitan monostearate, polysorbate 60, 2-octyldodecanol, benzyl alcohol, glycine, sorbic acid, potassium sorbate, disodium hydrogen phosphate, sodium chloride, and water.

The compositions may be prepared in any of a variety of forms suitable for the desired mode of administration. For example, pharmaceutical compositions may be prepared in the form of tablets, pills, powders, lozenges, sachets, cachets, elixirs, suspensions, emulsions, solutions, syrups, aerosols (as solids or in liquid media), ointments (e.g., containing up to 10% by weight of a cell-cycle control agent), soft-gel and hard-gel capsules, suppositories, sterile injectable solutions, sterile packaged powders, and the like.

Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation can be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an agent can be dissolved in an aqueous solution of an organic or inorganic acid, such as 0.3 M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, gylcerin and the like in concentrations ranging from 0–60% of the total volume. In an exemplary embodiment, a coumarin compound is dissolved in DMSO and diluted with water. The composition may also be in the form of a solution of a salt form of the active ingredient in an appropriate aqueous vehicle such as water or isotonic saline or dextrose solution.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include fillers such as sugars, including lactose, sucrose, mannitol, or sorbitol and cellulose preparations, such as maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gun arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

For administration to the eye, a microtubule stabilizing agent is delivered in a pharmaceutically acceptable ophthalmic vehicle such that the agent is maintained in contact with the ocular surface for a sufficient time period to allow the agent to penetrate the corneal and internal regions of the eye, including, for example, the anterior chamber, posterior chamber, vitreous body, aqueous humor, vitreous humor, cornea, iris/cilary, lens, choroid/retina and selera. The pharmaceutically acceptable ophthalmic vehicle may be an ointment, vegetable oil, or an encapsulating material. A microtubule stabilizing agent may also be injected directly into the vitreous and aqueous humor.

Alternatively, the active ingredient may be in powder form for constitution with a suitable vehicle, e.g., sterile pyrogen-free water, before use. The compounds may also be formulated in rectal compositions such as suppositories or retention enemas, e.g, containing conventional suppository bases such as cocoa butter or other glycerides.

In addition to the formulations described above, the compounds may also be formulated as a depot preparation. Such long-acting formulations may be administered by implantation, for example, subcutaneously, intramuscularly, or intraocularly, or by intramuscular injection. Thus, for example, the compounds may be formulated with suitable polymeric or hydrophobic materials, for example, as an emulsion in an acceptable oil, or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) comprises VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80, the fraction size of polyethylene glycol maybe varied, other biocompatible polymers such as polyvinyl pyrrolidone may replace polyethylene glycol, and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

The inventive agents may be prepared using the reaction routes and synthesis schemes as described below, employing the techniques available in the art using starting materials that are readily available. Other microtubule stabilizing agents may be prepared in manners analogous to the general procedures described above or the detailed procedures described in the examples herein.

The preparation of the coumarin compounds is described in detail herein, but the artisan will recognize that the chemical reactions described may be readily adapted to prepare a number of other microtubule stabilizing agents of the present invention. For example, the synthesis of non-exemplified compounds according to the invention may be successfully performed by modifications apparent to those skilled in the art, e.g., by appropriately protecting interfering groups by changing to other suitable reagents known in the art, or by making routine modifications of reaction conditions. Alternatively, other reactions disclosed herein or known in the art will be recognized as having applicability for preparing other compounds of the invention.

The coumarins of the present invention may be prepared by biosynthetic pathways. For example, in higher plants, coumarins are generally produced via the shikimate-chorismate biosynthetic pathway as a derivative of cinnamic acid, which is a precursor of many other natural products. The shikimate-chorismate pathway is also responsible for the formation of the aromatic amino acids. Phosphoryl group transfer from ATP followed by nucleophilic displacement results in the formation of 3-enolpyruvyl-shikimate-5-phosphate from shikimate, and the elimination of phosphate gives chorismate. The enzyme chorismate mutase then catalyses the rearrangement of chorismate to prephenate, which is converted to phenylpyruvate by means of a 1,4 elimination. A glutamate-dependent transamination results in the formation of phenylalanine. Phenylalanine is then converted to trans-cinnamic acid by the action of the enzyme phenylalanine ammonia-lyase, which eliminates NH3+.

From this point, simple coumarins which are oxygenated at C-7 follow a biosynthetic route different to those which are not oxygenated at this posision. In the latter case, the trans-cinnamic acid is first 2'-hydroxylated, then glucosylated to give trans 2'-glucosyloxycinnamic acid. This is then converted to the cis-isomer. Cis-2'-glucosyloxycinnamic acid (or coumarinyl glucoside) is the bound form in which coumarin exists in plants. The hydroxylation and glucosylation of the trans-cinnamic acid are enzyme catalyzed reaction. The trans-cis isomerisation is mediated by UV light. The 7-oxygenated simple coumarins arise as a result of para-hydroxylation rather than ortho-hydroxylation. As in the previous reaction scheme, a glucosylation reaction is also involved, followed by UV-dependent trans-cis isomerisation.

The coumarins of the present invention may be prepared by chemical synthesis. For example, the Perkin reaction is the classical reaction for the formation of coumarin and involves the heating of o-hydroxybenzaldehyde with sodium acetate and acetic anhydride at 180° C. The synthesis of simple coumarins with methoxy or hydroxy groups may be prepared by the Perkin reaction, despite poor yields. The formation of the pyrone ring is an important step in the chemical synthesis of several coumarin compounds and several methods have been developed to introduce functional groups into the basic coumarin structure. One strategy for synthesis may include preparing a phenol which contains the desired substituents of the coumarin before the pyrone ring is formed. Alternatively the basic coumarin structure may be synthesized first and C- or O-alkylation or nuclear oxygenation can be employed to produce the desired compound. See COUMARINS: BIOLOGY, APPLICATIONS AND MODE OF ACTION. R. O'Kennedy and R. D. Thornes. 1997. John Wiley and Sons. Chichester.

3,6,7-trihydroxycoumarin may be isolated from algae. For example, algal samples of *Dasycladalus vermicularis* from purified cultures of and from natural habitats are briefly rinsed in distilled water. After removal of excess water with a tissue paper, the algae are weighed and immersed in a solution of 50% acetone and 50% methanol. About 100 g (fresh weight) of the sample is collected in acetone, cut into small pieces and extensively ground with quartz sand in a mortar. See Menzel, D., et al. (1983) Botanica Marina 26: 23–29, which is herein incorporated by reference. The extract is filtered and the remaining material is repeatedly extracted until 1 L of acetone is utilized.

The combined extracts are concentrated in vacuo at 30° C. until all lipophilic pigments are precipitated until about 1 ml to about 2 ml of a clear, yellow aqueous extract remains. Hydrolysis is employed in $0.5_N$ HCl (final concentration) at 100° C. for about 5 to about 30 minutes. The coumarin compounds are extracted from the hydrolysis mixture with chloroform or ethylacetate and evaporated to dryness. Subsequent chromatography may be carried out on cellulose thin layer plates and developed with dual solvent systems to yield maximal isolation and resolution. Once the presence of the coumarin compounds has been established, RP-HPLC is utilized for high-resolution purification and isolation. A protocol for the simultaneous determination of phenolic compounds has been established by Andrade et al. ((1998) Journal of Liquid Chromatography & Related Technologies 21(18):2813–2820, which is herein incorporated by reference) and may be used. The structures of the various simple coumarin precursors and analogs may be determined by mass spectroscopy and where necessary by $H^1$ NMR. See Menzel, D., et al. (1983) Botanica Marina 26:23–29.

In the following Examples, all reagents were obtained from Sigma (St. Louis, Mo.).

EXAMPLE 1

The Effects of Coumarin Compounds on Dividing Sea Urchin Embryos

A. Inhibition of Cell Division

Male and female *Strongylocentrotus purpuratus* or *S. franciscanus* were injected with 0.5 M KCl through the soft tissue of the oral surface into the coleomic cavity and were then cultured in filtered seawater by conventional methods in the art. See e.g. O'Brien, E. T., et al. (1989) Mol. Pharmacol. 35:635–642; and Jacobs, J. S. and L. Wilson (1986) Drugs Pharm. Sci. 27:481–493, which are herein incorporated by reference. Gametes were released into filtered seawater. The eggs were stirred and passed 3 times through a 150 mm Nitex mesh (Tetko, Inc., Elmsford, N.Y.) to remove the jelly coating and then allowed to settle. The seawater was aspirated off and then the eggs were centrifuged for 4 minutes at 310 rpm. The eggs were resuspended at 1% (v/v) in filtered seawater and set aside. Fresh sperm were collected from the aboral surface of a male urchin. About 1 drop of concentrated sperm was collected into a test tube and 1 ml of seawater was added. A 1 ml aliquot of the sperm solution was added per 100 ml of suspended eggs and immediately mixed.

After 1 minute post-fertilization, about 1 ml of embryos were placed on a microscope slide and checked for percent fertilization under a 10× magnification with a light microscope. A visible fertilization membrane differentiates fertilized egg from the unfertilized. The fertilized embryos were then incubated with a coumarin compound no later than 5 minutes after initial fertilization. The embryos were incubated for about 2 hours at about 15° C. to about 17° C., or until the control embryos completed first division and were in the 2-cell stage. The amount of division was calculated in each test sample by counting the number of divided versus undivided embryos in a small sample of about 40 $\mu$L using the light microscope.

Quantitation of division was performed by counting the number of divided and nondivided embryos after the control embryos had progressed to the end of first cleavage (about 120 minutes after fertilization). Compounds which inhibit first cell cleavage by 50% or more at concentrations of about 50 $\mu$M were used for further studies in microtubule polymerization assays.

As shown in FIGS. 1–4, coumarin, 7dicoumarol, umbelliferone, and warfarin, inhibited the first cleavage of *S. purpuratus* embryos. Dicoumarol was the most potent as the first cleavage was inhibited by about 50% at about 4 $\mu$M dicoumarol and cell division was completely blocked at concentrations of about 20 $\mu$M or more. The dicoumarol treated embryos showed no lysis or morphological changes. Dose-response curves obtained for *Lytechinus pictus* and *S. franciscanus* embryos were identical to those obtained using *S. purpuratus,* thereby indicating that the activity of dicoumarol is not limited to a particular species of echinoder embryo.

B. Cell Cycle Analysis

The effect of coumarin compounds, such as dicoumarol, at different stages of the cell cycle was determined by adding dicoumarol at 10-minute intervals after fertilization to aliquots of sea urchin embryos and observing the percentage of inhibition of the first cleavage. Specifically, aliquots were designated T-10, T-20, . . . T-120. At 10 minutes after fertilization, 50 $\mu$M of dicoumarol was added to the aliquot designated T-10, at 20 minutes after fertilization, 50 $\mu$M of dicoumarol was added to the aliquot designated T-20, and so on.

Figure 5:
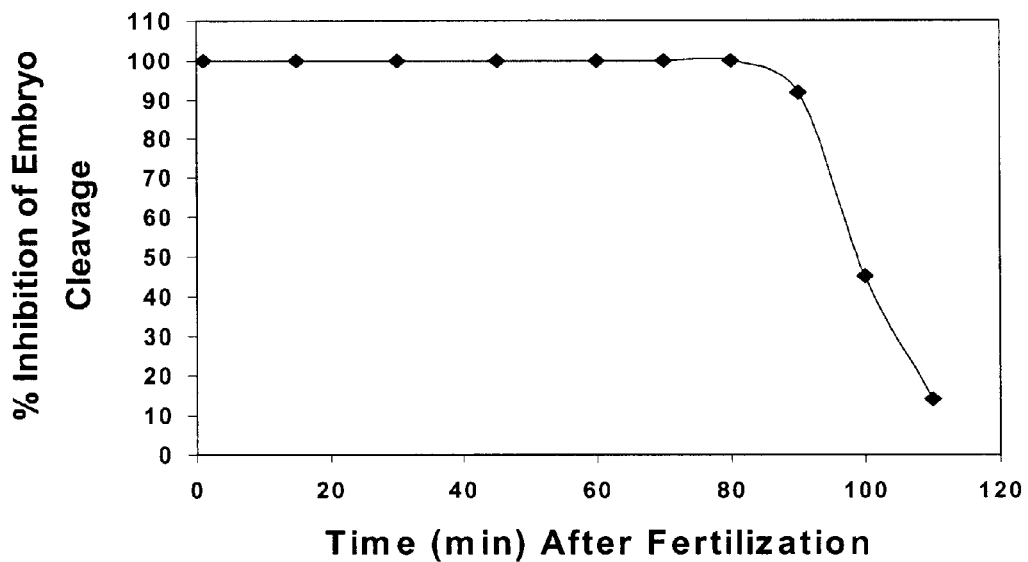
FIG. 5 illustrates the % inhibition of embryo cleavage at different times after fertilization.

As shown in FIG. 5, the inhibition of cell cleavage rapidly declined when dicoumarol was added 90 minutes after fertilization, thereby indicating that dicoumarol inhibits cell division by blocking cells in pro-metaphase or metaphase of mitosis and that the mode of action does not affect events occurring during the first 90 minutes of development, such as DNA synthesis.

EXAMPLE 2

The Effect of Coumarin Compounds on Spindle and Chromosome Organization

To determine the effect of coumarin compounds on spindle microtubule organization and chromosome organization sea urchin embryos and HeLa cells were studied.

A. Sea Urchin Embryo Assays

Sea urchin embryos prepared according to Example 1 were used to study the effect of coumarin compounds on spindle microtubule organization and chromosome organization using immunofluorescence microscopy with specific antibodies for tubulin and DAPI was used to image the chromatin. Two different sea urchin embryo assay protocols were used. The modified protocol of Hollenbeck and Cande as described at A1 below was found to be less reliable, and thus less desirable as the modified method of Balczon and Schatten as described at A2 below.

A1. Modified Hollenbeck and Cande Assay

Fixation and staining of embryos for immunofluorescence microscopy were performed according to the method of Hollenbeck and Cande ((1985) European Journal of Cell Biology 37:140–148) with the following the modifications of O'Brien, E. T., et al. ((1989) Molecular Pharmacology 35:635–642), both of which are incorporated by reference. Embyros were gently pipetted onto air-dried polylysine-coated (1 mg/ml) coverslips and allowed to adhere for about 2 minutes. The coverslips were drained and immediately placed into small weigh boats containing 2 ml of PIPES extraction buffer comprising 0.4% Triton X-100 in 50 mM PIPES, 10 mM EGTA, 6 mM $MgSO_4$, pH 6.8.

After about 4 to about 5 minutes, the coverslips were fixed in 1% (w/v) paraformaldehyde, 1% (w/v) glutaraldehyde, in PIPES extraction buffer, for 10 minutes. The coverslips were washed three times with a solution of PBS, (137 mM NaCl, 2.7 mM KCl, 8 mM sodium phosphate, 1.5 mM potassium phosphate, pH 7.5), followed by two 5-minute washes with a 4 mg/ml solution of sodium borohydride in PBS, to decrease aldehyde fluorescence. The coverslips were then washed three times with PBS and 25 µl of mouse monoclonal anti-alpha-tubulin, diluted 1/100 in PBS, was added to each coverslip. The coverslips were incubated at 37° C. for 60 minutes and washed three more times with PBS. A 25-µl volume of a secondary staining solution was then added, which comprised a fluoroscein isothiocyanate conjugated to an anti-mouse IgG (1/25 in PBS) to stain the microtubules, rhodamine-conjugated phalloidin (1/20 in PBS) (Molecular Probes) to stain the actin filaments and DAPI (10 µg/ml) to stain the chromatin and chromosomes. The coverslips were then incubated for an additional 60 minutes at 37° C. and washed three times with PBS. The coverslips were mounted onto slides with a solution of 0.1 M sodium borate, pH 8.0 and sealed with clear nail polish. The slides were stored at 4° C. in the dark until used.

The fixed and stained embryos were viewed with a Zeiss Photomicroscope III, using Plan-Neofluor 25× and 40× objectives. Embryos were photographed using Kodak technical Pan film at 200 or 800 ASA film speed.

A2. Modified Balczon and Schatten Assay

Fixation and staining of embryos for immunofluorescence microscopy were performed according to a modified method of Balczon and Schatten ((1983) Cell Motility 3:213–226, which is herein incorporated by reference). At various times, 60, 70, 80, 90, 100, and 110 minutes, after 10 µL of 5 mM dicoumarol was added (until a final concentration of 50 µM dicoumarol was obtained), a concentrated suspension of *S. franciscanas* embryos prepared according to Example 1 was gently pipetted into 12×75 mm glass tubes, and the seawater was replaced with an extraction buffer comprising 0.55 mM $MgCl_2$, 10 mM EGTA, 25 mM MES, 25% glycerol, 1% Nonidet P-40, and 25 µM PMSF, pH 6.7. After extraction for 45 minutes, the embryos were fixed for 6 minutes with −10° C. methanol. After methanol fixation, the cells were rinsed for 5 minutes in PBS and then 25 µl of anti-α-tubulin monoclonal antibody (1:100) in PBS comprising 2% bovine serum albumin was added.

The embryos were incubated at 37° C. for about 60 to about 75 minutes and rinsed for 20 minutes in PBS after which 25 µl of a secondary staining solution comprising fluoroscein isothiocynate (FITC) conjugated to an anti-mouse IgG (1:100 in PBS) and DAPI (10 µg/ml) was added. The embryos were then incubated for 60 minutes at 37° C. and then rinsed for 20 minutes in PBS. Coverslips were mounted onto the slides with a solution of Vectashield® (Vector Laboratories, Inc., Burlingame, Calif.) and sealed with nail polish. The slides were stored at 4° C. in the dark until further use.

The fixed and stained embryos were viewed with a Zeiss Photomicroscope III, using Plan-Neofluor 25× and 40× objectives. Embryos were photographed using Kodak technical Pan film at 200 or 800 ASA film speed.

Figure 14A:
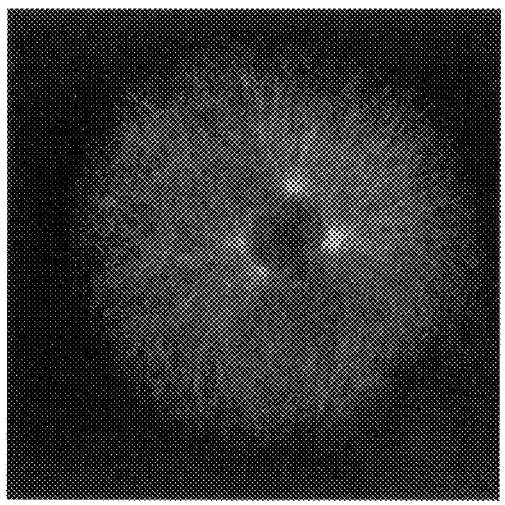
FIG. 14 shows chromosomes in sea urchin embryo control cells at 70, 80, 90, 100, and 110 minutes.
Figure 14B:
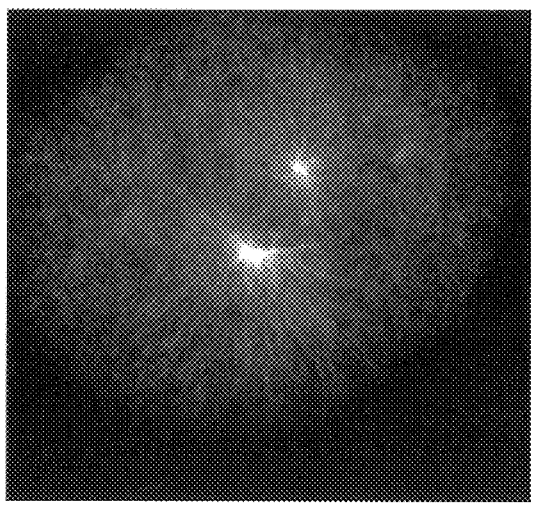
Figure 15:
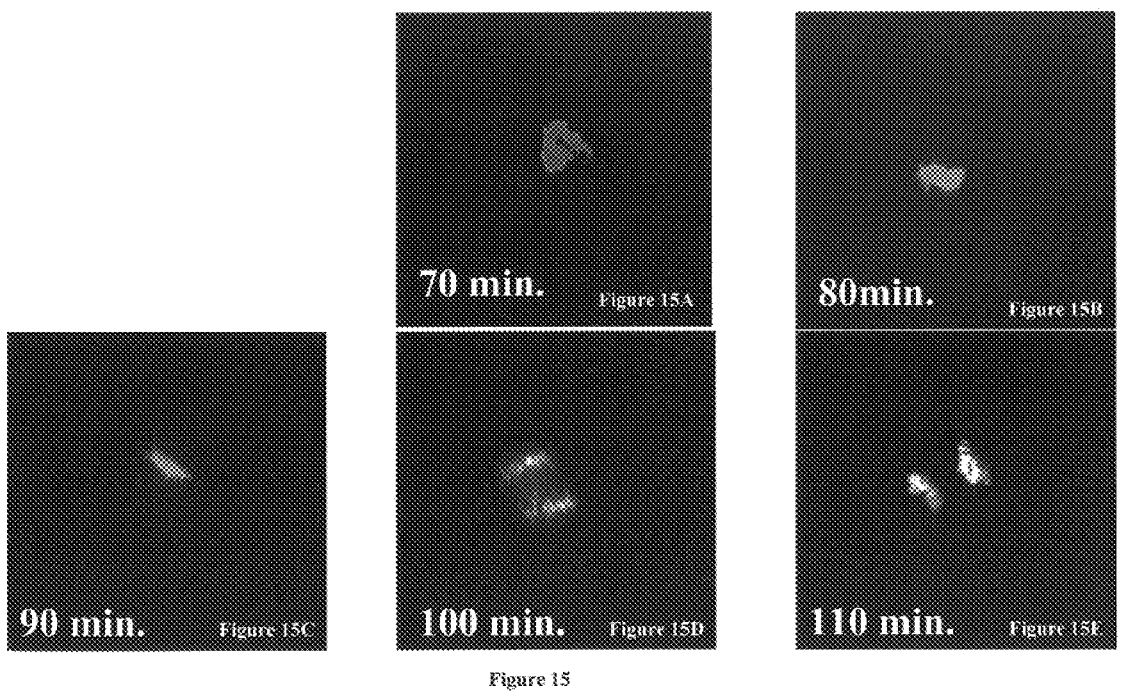
FIG. 15 shows microtubules in sea urchin embryo cells treated with 50 $\mu$M dicoumarol.
Figure 16:
FIG. 16 shows chromosomes in sea urchin embryo cells treated with 50 $\mu$M dicoumarol.

Examination of microtubule organization showed control cells at metaphase with bipolar spindles with compact chromosomes condensed at the metaphase plate. See FIGS. 13 and 14. FIG. 15 illustrates the effects of dicoumarol on cellular microtubules at mitosis. At 50 µM dicoumarol, the microtubules of mitotic spindles were bipolar, but appeared to be longer and located outside an intact nuclear envelope. The dicoumarol treated cells contained disorganized chromosomes that had not congressed to the metaphase plate. See FIG. 16. The microtubules and chromosomes of the dicoumarol treated sea urchin embryo cells appeared the same at 90, 100, and 110 minutes.

B. HeLa Cell Assay

HeLa cells were fixed in formalin followed by methanol. Tubulin was detected with a mouse monoclonal antibody that is specific for b-tubulin in HeLa cell extracts and chromosomes were stained with DAPI (4,6-diamino-2-phenylindole). Second antibodies were fluorescein isothiocyanate-conjugated goat anti-mouse IgG and rhodamine-conjugated goat anti-human IgG. The percentage of cells arrested in metaphase were counted on preparations double-stained with DAPI and then for anti-tubulin immunoflourescence. At least 400 cells were counted at each drug concentration tested. At drug concentrations, varying from about 1 µM to about 100 µM, that were just sufficient to induce metaphase arrest, metaphase was clearly distinguishable from other stages of mitosis by the presence of a characteristic compact metaphase plate of chromosomes. Photomicrographs were obtained using a Zeiss Photomicroscope III equipped with an epi-fluoresence condenser and a 100× Olympus UVFL oil immersion objective as described previously by Jordan et al. (1991) Cancer Res. 51(8): 2212–2222, which is herein incorporated by reference.

EXAMPLE 3

Determination of Microtubule Polymer Mass

Bovine brain microtubule protein and phosphocellulose purified tubulin were isolated and stored as frozen pellets at 70° C. Specifically, microtubule protein was isolated from bovine brain by three cycles of warm polymerization and cold depolymerization in vitro. See Farrell and Wilson (1984) Biochem. 23:3741–3748, which is herein incorporated by reference. Microtubules of mammalian cells disintegrate at temperatures below about 10° C. and reconstitute from tubulin in vitro at physiological temperatures in the presence of GTP and magnesium ions.

On the basis of the reversibility of cold-induced microtubule disassembly, tubulin can be purified by a temperature dependent disassembly/reassembly cycle that includes cooling microtubule suspensions, separation of non-microtubule material by high-speed centrifugation, re-warming after addition of GTP and magnesium, and sedimentation of reassembled microtubules. After 3 cycles, a pure preparation of tubulin is obtained.

Tubulin was purified from the microtubule protein by phosphocellulose chromatography using a 1 L 0.5N NaOH phosphocellulose (PC) column. The tubulin solution was quickly frozen as drops in liquid nitrogen and stored at −70° C. until used. The protein concentration was determined by the method of Bradford using bovine serum albumin as the standard. See Bradford, M. M. (1976) Anal. Biochem. 72: 248–354, which is herein incorporated by reference.

Tubulin pellets were thawed and mixed with *Stronglycocentrotus purpuratus* flagellar axonemal seeds in 87 nM 1,4-piperazinediethanesulfonic acid (PIPES), 36 mM 2-morpholinoethanesulfonic acid (Mes), 1.8 mM $MgCl_2$, 1 mM EGTA, pH 6.8 (PMME buffer) and 2 mM GTP and then polymerized to steady state by incubation for about 35 to about 45 minutes at 37° C. Axoneme "seeds" were prepared according to Toso et al (1993) Biochem. 32(5):1285–1293, which is herein incorporated by reference. Following polymerization, the microtubules were separated from unpolymerized tubulin by centrifugation at 150,000×g for 1 hour. The protein concentration of the supernatant after centrifugation was determined by the Bradford method. The quantity of sedimented microtubule protein was determined by comparing the supernatant protein concentration to that sedimented by 1 mM GTP (final concentration).

Polymerization of microtubules in the presence of low concentrations of dicoumarol (less than about 10 $\mu$M) had no significant effect on the mass of polymer formed as compared with controls. At 50 $\mu$M dicoumarol, the polymer mass was increased by about 16%. See FIG. 10. It was found that dicoumarol concentrations of greater than about 100 $\mu$M significantly induced polymerization. Various dicoumarol concentrations did not, however, significantly increase the presence of axonemal seeds.

EXAMPLE 4

Turbidity (Polymerization) Assay

To determine the rate and extent of the ability of a test compound to promote or inhibit microtubule polymerization (change in turbidity) a coumarin compound is added to a cuvet comprising about 1 mg/ml microtubule protein. The cuvet is incubated at 37° C. for 45 minutes in a spectrophotometer equipped with a heating unit and the absorbance is measured at about 340 nm. The change in absorbance is measured at intervals of 45 seconds over the 45-minute period and compared to the absorbance change induced by 1 mM GTP.

Specifically, 1.2 mg/ml of microtubule protein was mixed with different concentrations of dicoumarol in 100 mM PIPES, 1 mM $MgCl_2$, and 1 mM EGTA (100 mM PEM buffer), and 1 mM guanosine 5'-triphosphate. Microtubule polymerization was monitored at 37° C. by light scattering at 350 nm using a Gilford Response Spectrophotometer.

As shown in FIG. 9, dicoumarol increased the rate and extent of tubulin polymerization (12 $\mu$M) in a concentration-dependent manner. The increase in turbidity was gradual, and after about 1 hour of incubation, steady state was not reached.

10 $\mu$l aliquots were taken from spectrophotometrically followed reaction mixtures obtained during the course of the turbidity/light scattering assays at 10, 20, and 45 minutes and applied to 200-mesh carbon coated, Formavar-treated, copper grids (Ted Pella, Inc., Redding, Calif.). The sample was followed by several drops of 0.5% uranyl acetate and excess was drained off with filter paper. The grids were then examined with a Zeiss model 10CA electron microscope.

To determine the length of microtubules, at desired times, 10 $\mu$l aliquots are taken and diluted 40-fold with 0.2% glutaraldehyde at 30° C., and the microtubules are allowed to adhere to colloidion film on copper grids (Ted Pella, Inc., Redding, Calif.) for 30 seconds. The grids are treated with a 0.1% solution of cytochrome c for 15 seconds, rinsed with water, and negatively stained with 1% uranyl acetate. Photographic prints are prepared at a final magnification of 6000×. A MOP-3 image processor is utilized to accumulate and process the length data, and the number of microtubules for each sample is counted.

EXAMPLE 5

Binding Assays Utilizing Fluorescence Measurements

To determine the binding constant of dicoumarol to tubulin, fluorescence measurements were performed using a Perkin-Elmer LS50B spectrofluorometer. Spectra were taken by multiple scans and buffer blanks were subtracted from all measurements. The inner filter effects were corrected as described by Sackett, D. L. ((1995) Biochemistry 34:7010–7019, which is herein incorporated by reference) and empirically by measuring the change of fluorescence intensity of a tryptophan solution equivalent to the tubulin concentration in the presence of dicoumarol. See Lee, J. C., et al. (1975) J. Biol. Chem. 250:9276–9282, which is herein incorporated by reference. Dicoumarol did not quench the fluorescence of tryptophan in solution after inner filter effect correction. The excitation and emission wavelengths were 295 nm and 336 nm, respectively.

Specifically, 2 $\mu$M tubulin was incubated with various concentrations of dicoumarol, 0, 5, 10, 15, 20, 25, 30, 40, and 50 $\mu$M, for 30 minutes at 34° C. in 50 mM PEM buffer and then analyzed. The fraction of binding sites ($\beta$) occupied by dicoumarol was determined using the following relationship: $\beta=(F_0-F)/(F_0-F_m)$, wherein $F_0$ is the fluorescence intensity of tubulin in the absence of dicoumarol, F is the corrected fluorescence intensity when the tubulin and dicoumarol are in equilibrium, and $F_m$ is the calculated fluorescence intensity of the fully liganded tubulin. $F_m$ was determined by plotting $1/(F_0-F)$ versus 1/L(L=total ligand concentration) and extrapolating 1/L=0. The association constant, $K_a$, was determined using the relationship: $K_a=(\beta/1-\beta)\times 1/Lf$, where Lf=L [C] and [C] is the molar concentration of ligand binding sites assuming a single binding site per tubulin dimer.

Dicoumarol was found to quench the intrinsic fluorescence of tubulin in a concentration-dependent manner. The binding constant of dicoumarol to tubulin was calculated to be 8.72, thereby indicating that dicoumarol binds strongly to the tubulin dimer.

EXAMPLE 6

Stoichometry of Coumarin Binding to Microtubules

To determine the stoichiometry of coumarin compound binding to microtubules, about 13 $\mu$M of tubulin is polymerized at the ends of axonemal seeds in the presence of different concentrations of coumarin containing a trace amount of [$^3$H]coumarin. Unbound coumarin is separated from microtubules by centrifugation through 50% sucrose cushions for 75 minutes at 37° C. at 190,000×g. Microtubule pellets are solubilized in PMME buffer comprising 87 mM PIPES, 36 mM MES (2-[N-Morpholino]ethanesulfonic acid), 1.4 mM $MgCl_2$, and 1 mM EGTA, pH 6.8 at 0° C., the tubulin concentration in the pellets is determined and the amount of coumarin bound to microtubules is determined by scintillation counting. The molar amount of coumarin bound per mole of tubulin dimer in the microtubules is determined by dividing the coumarin concentration by the tubulin concentration in the polymer. The mean lengths of the microtubules are determined by video microscopy and the number of coumarin molecules bound per microtubule was calculated by using a value of 1,690 tubulin dimers per $\mu$m of microtubule length. The binding stoichiometry is calculated in terms of the number of microtubules in suspension and plotting the data as a double-reciprocal plot. A low maximum stoichiometry of coumarin binding to microtubules suggests that coumarin binds at the microtubule ends.

EXAMPLE 7

Inhibition of [$^3$H]paclitaxel Binding to Polymer

To determine how coumarin compounds affect the binding of taxol to tubulin polymers, the following competitive inhibition assay may be conducted. For all binding studies, tubulin polymer is preformed in the absence of a given coumarin compound for about 30 minutes at 37° C. in reaction mixtures comprising about 2 $\mu$M tubulin, about 20 $\mu$M ddGTP, and about 0.75 M monosodium glutamate. Mixtures of the given coumarin compound with [$^3$H] paclitaxel in varying concentrations are added to the preformed polymer and incubated for about 30 minutes at 37° C. Bound [$^3$H]paclitaxel is separated from free paclitaxel by centrifugation of the reaction mixtures at 14,000 rpm in an eppendorf microfuge for about 20 minutes at room temperature. Protein and radiolabel in both supernatants and pellets (dissolved in 0.1 M NaOH overnight and neutralized with 0.1 M HCL) are quantified according to the procedure of Lowry and liquid scintillation counting. A competitive inhibitor of the binding of [$^3$H]paclitaxel to the polymer will provide a family of parallel curves at different inhibitor concentrations (in Hanes format). If a given coumarin compound competitively inhibits the binding of taxol to tubulin polymers, the coumarin compound and taxol may have a common tubulin polymer binding site.

EXAMPLE 8

Critical Concentrations of Tubulin for Assembly with Coumarin Compounds

Critical concentrations of tubulin for assembly with a given coumarin compound may be measured in reaction mixtures comprising about 10 $\mu$M of the given coumarin compound, 4% dimethyl sulfoxide, 0.1M MES (pH 6.9) and 100 $\mu$M GTP and MAPs (microtubule associated proteins) at half the concentration in mg/ml of tubulin. Critical concentrations are determined from final turbidity readings at 350 nm, with turbidity plotted against tubulin concentration. The critical concentration is taken as the intercept on the concentration axis.

Microtubule polymers are considered stable only if the subunit concentration exceeds the concentration required for nucleation the subunit concentration required for stable nuclei to form is termed the critical subunit concentration. The critical concentration is either the minimum concentration of subunit at which polymer exists or the steady state concentration of subunit. The critical concentration is determined by measuring the polymer content as a function of the total protein concentration and using the extrapolated protein concentration at zero polymer content as the critical concentration.

Specifically, an amount, such as 1.2 mg/ml, of microtubule protein is mixed with different concentrations of dicoumarol such as 0 $\mu$M, 10 $\mu$M, 20 $\mu$M, 50 $\mu$M, and 100 $\mu$M dicoumarol, in 100 mM PIPES, 1 mM $MgCl_2$, and 1 mM EGTA (100 mM PEM buffer), and 1 mM guanosine 5'-triphosphate. Microtubule polymerization was monitored at 37° C. by light scattering act 350 nm using a spectrophotometer conventional in the art, such as a Gilford Response Spectrophotometer.

EXAMPLE 9

Analysis of Steady-State Dynamic Instability Parameters of Individual Microtubules by DIC Video Microscopy Analysis of dynamic instability behavior of individual microtubules at steady state was conducted with real-time DIC video microscopy as described by Walker et al. (1988) J. Cell Biol. 107:1437–1448 and Panda et al. (1995) Biochem 34:9921–9929, both of which are herein incorporated by reference. A Hamamatsu C2400 Newvicon video camera was used to capture the images of microtubules which were enhanced with a Hamamatsu DVS3000 digital image processor. Analysis of length changes was performed using a video analysis software program designed by N. Gliksman at the University of North Carolina.

Microtubules were grown at the ends of sea urchin flagellar axonemal fragments (seeds) to distinguish the plus and minus ends. The microtubules were allowed to achieve polymer-mass steady state which took less than about 30 minutes, and analysis of the steady-state dynamics was carried out for about 30 minutes to about 45 minutes without deterioration of the microtubules or any detectable changes in dynamics. The individual dynamic instability parameters were analyzed quantitatively. These included the rates of growing and shortening, the lengths of time microtubules grow and shorten, the mean lengths of each growing or shortening event, the transition frequencies from the growing or attenuated state to shortening or from shortening to the growing or attenuated or paused state, the percentage of total time the microtubules spend growing, shortening, or in the attenuated state, and the overall dynamicity, the combined total observable growing and shortening per unit time. See Kowalski, R. J. et al. (1993) 26(4):282–290, which is herein incorporated by reference.

Tubulin pellets were thawed and centrifuged at 4° C. to remove any aggregated or denatured tubulin. The purified tubulin was mixed with axoneme seeds and polymerized in PMME buffer (87 mM PIPES, 36 mM MES, 1.4 mM $MgCl_2$, 1 mM EGTA, pH 6.8) comprising 1 mM GTP in the presence or absence of coumarin compounds. Alternatively, the purified tubulin (17 $\mu$M) was added to *S. purpuratus* flagellar axonemal seeds in PME buffer (75 mM PIPES, 1.8 mM $MgCl_2$, 1 mM EGTA, pH 6.8) comprising 1.5 mM GTP and incubated to steady state for about 35 to about 45 minutes at 37° C. in the presence or absence of various dicoumarol concentrations (about 0.04 $\mu$M to about 50 $\mu$M).

The seed concentration was adjusted to achieve about 3 to about 6 seeds per microscope field. After 35 minutes of incubation, samples of microtubule suspensions (2.5 $\mu$l and 2.0 µl) were prepared for video microscopy, and the dynamics of individual microtubules were recorded at 37° C. as described previously (Panda et al. (1995) Biochem. 34:9921–9929, which is herein incorporated by reference).

The microtubules were observed for a maximum of 45 minutes after reaching steady state. The microtubule was determined to be in a growing phase if the microtubule increased in length by >0.2 µM at a rate >0.15 µm/min and in a shortening phase if the microtubule shortened in length by >0.2 µM at a rate >0.3 µm/min. Length changes equal to or less than 0.2 µm over the duration of six data points were considered as attenuation phases. The same tubulin preparation for all experiments was used and for preliminary experiments, an average of about 10 to about 15 microtubules was measured for each experimental condition, and for the results provided in Table 1, about 20 to about 30 microtubules were analyzed for each experimental condition.

The catastrophe frequency (transition from the growing or attenuated state to shortening) was calculated by dividing the number of catastrophes by the sum of the total time spent in the growing plus attenuated states for all microtubules for a particular condition. The rescue frequency (transition from shortening to growing or attenuation, excluding new growth from a seed) was calculated by dividing the total number of rescue events by the total time spent shortening for all microtubules for a particular condition. Control microtubules alternated between phases of growing and shortening, but also spent a small percentage of time in an attenuated state.

Figure 17A:
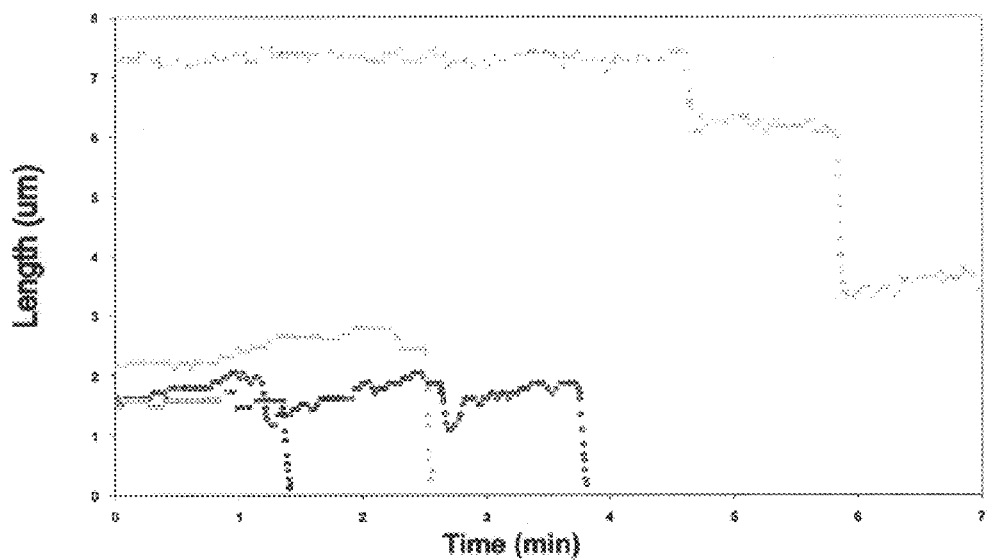
FIG. 17A shows the length changes of individual control microtubules at plus ends.
Figure 17B:
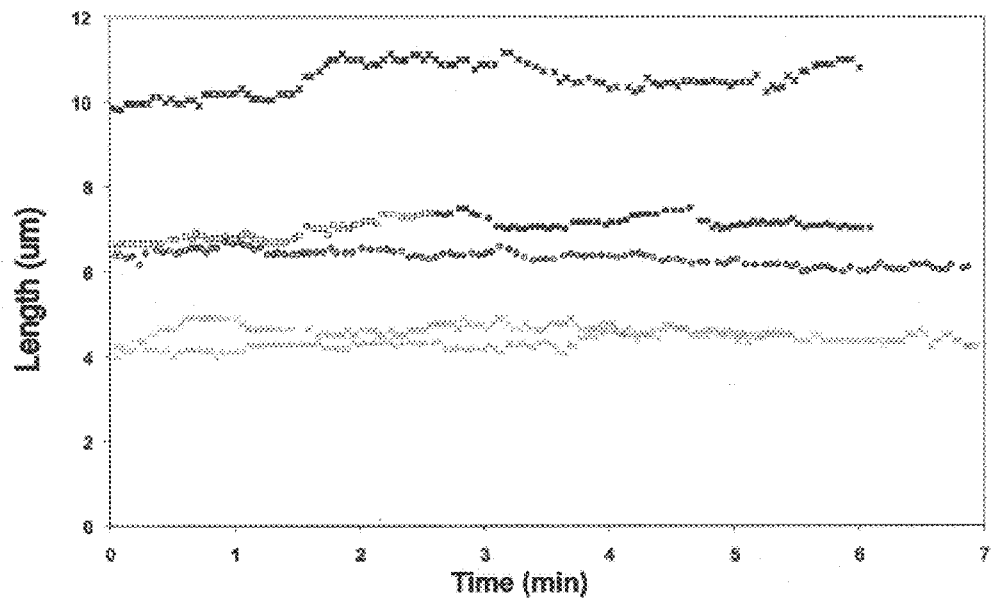
FIG. 17B shows the length changes of individual microtubules at plus ends in the presence of dicoumarol.

In preliminary experiments with coumarin compounds at microtubule plus ends, micromolar concentrations of dicoumarol were found to stabilize dynamic instability behavior as shown in FIG. 17. As shown in FIG. 17A, there are five traces of individual control microtubules growing and shortening with time. Each symbol represents an individual microtubule. The effects of 1 µM dicoumarol on the growing and shortening dynamics of six individual microtubules are shown in FIG. 17B.

Further experiments confirmed that dicoumarol significantly depresses dynamics at microtubule plus ends. The effects of the dicoumarol concentrations ranging from 0.04 µM to 50 µM on the parameters of dynamic instability show that dicoumarol inhibits the rate and extent of microtubule shortening in a concentration-dependent manner.

Specifically, the addition of 1 µM dicoumarol significantly reduced the mean shortening rate by about 58%, from about 18.5 µM per minute to about 7.8 µm per minute, and reduced the lengths of a shortening excursion by about 40% from about 2.3 µM to about 1.4 µM. In contrast to the strong action of dicoumarol on the rates and lengths of shortening, there was no significant change in the average rate or lengths of growth at various dicoumarol concentrations. At concentrations as low as 0.1 µM, dicoumarol significantly increased the overall percentage of time in the attenuated state from by 63%. In contrast, there was no significant effect of dicoumarol on the total time spent growing. Dicoumarol decreased the frequency of catastrophe by about 65% (from 0.62 to 0.22 µM) at concentrations as low as 0.1 µM. Dicoumarol also decreased the dynamicity by about 57% at a concentration of 0.1 µM.

Thus, coumarin compounds, such as dicoumarol, significantly decrease the dynamic behavior of microtubules primarily by inhibiting the rate and extent of microtubule shortening and decreasing the catastrophe frequency.

EXAMPLE 10

Tubulin Exchange with Radiolabeled GTP

Since soluble tubulin binds GTP reversibly at an exchangeable site in beta-tubulin and the GTP become nonexchangeably incorporated as GDP when the tubulin becomes incorporated at the growing microtubule ends, the following method may be used to analyze tubulin exchange dynamics at a molecular level at the combined microtubule ends using [$^3$H]GTP or simultaneously at both microtubule ends with a double-label strategy under conditions in which treadmilling rather than dynamic instability is the predominant behavior. See, e.g., Farrell et al. (1987) J. Cell Biol. 184:1035–1046, which is herein incorporated by reference.

Analysis is carried out in combination with determinations of mean microtubule lengths and length distributions by electron- or DIC microscopy so that the exchange rates or extents can be analyzed per microtubule end. Incorporation of radiolabeled GDP and the protein content of the microtubules are quantitated after stabilizing the microtubules and collecting them by rapid filtration on glass-fiber filters, by sedimenting them through sucrose cushions or glycerol cushions. Because the analysis is carried out in microtubule suspensions, the measurements reveal the average incorporation or loss rates or extents at the ends of all microtubules present in the suspension rather than the rates or extents of incorporation at the ends of individual microtubules. Specifically, when a steady-state microtubule population is pulsed with radiolabeled GTP, an initial kinetically rapid burst of radiolabel incorporation is followed by a much slower linear rate of label incorporation. A similar rapid burst of radiolabel loss followed by a much slower linear rate of label loss occurs if microtubules are first assembled to steady-state in the presence of radiolabeled GTP and then chased with excess unlabeled GTP. The initial burst of radiolabel gain or loss is a measure of the extent of dynamic instability behavior at the microtubule ends while the slower linear rate of incorporation during a radiolabeled GTP pulse or loss of radiolabel from fully-labeled microtubules is a measure of the treadmilling rate.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A method of stabilizing microtubules in a subject comprising administering at least one coumarin compound or a derivative thereof to the subject.

2. The method of claim 1, wherein the subject is a cell or organism.

3. The method of claim 2, wherein the organism is a mammal.

4. The method of claim 3, wherein the mammal is human.

5. The method of claim 1, wherein the coumarin compound is coumarin, dicoumarol, 7-hydroxycoumarin (umbelliferone), 6,7-dihydroxycoumarin (esculetin), 3,6,7 trihydroxy coumarin, warfarin, or warfarin sodium.

6. A method of modulating microtubules in a subject comprising administering at least one coumarin compound or a derivative thereof to the subject.

7. The method of claim 6, wherein the subject is a cell or organism.

8. The method of claim 7, wherein the organism is a mammal.

9. The method of claim 8, wherein the mammal is human.

10. The method of claim 9, wherein the coumarin compound is coumarin, dicoumarol, 7-hydroxycoumarin (umbelliferone), 6,7-dihydroxycoumarin (esculetin), 3,6,7 trihydroxy coumarin, warfarin, or warfarin sodium.

11. The method of claim 1, wherein the coumarin compound is administered in the form of a pharmaceutical composition which further comprises a pharmaceutically acceptable salt or prodrug thereof, at least one supplementary compound, and a pharmaceutically acceptable excipient.

12. The method of claim 11, wherein the supplementary compound is an antineoplastic agent, an antiproliferative agent, an anti-inflammatory agent, or an anti-fungal agent.

13. The method of claim 11, wherein the supplementary compound is taxol, estramustine, taxotere, vinblastine, vincristine, discodermolide, griseofulvin, or amphotericin B.

14. The method of claim 1, wherein stabilizing the microtubules in the subject treats, prevents, or inhibits a disease or disorder associated with microtubule formation or microtubule function in the subject.

15. The method of claim 14, wherein the disease or disorder is a hyperproliferative or cystic disease.

16. The method of claim 14, wherein the disease or disorder is cancer, Alzheimer's disease, atherosclerosis, restenosis, or gout.

17. The method of claim 1, wherein stabilizing the microtubules modulates the cell cycle of a cell in the subject.

18. The method of claim 1, wherein stabilizing the microtubules treats, prevents, or inhibits cancer in the subject.

19. The method of claim 18, wherein the coumarin compound is not coumarin, 7-hydroxycoumarin, warfarin, or warfarin sodium.

20. The method of claim 1, wherein stabilizing microtubules treats, prevents, or inhibits a disease or disorder associated with microtubule formation or microtubule function in the subject and the coumarin compound has a basic structural formula

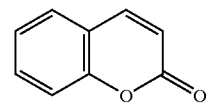

for a backbone structure, wherein the benzene ring, the pyrone, or both may further comprise at least one substituent.

21. The method of claim 1, further comprising administering an antineoplastic agent, an antiproliferative agent, an anti-inflammatory agent, or an anti-fungal agent.

22. The method of claim 1, further comprising administering a supplementary compound.

23. The method of claim 22, wherein the supplementary compound is a taxol, estramustine, taxotere, vinblastine, discodermolide, griseofulvin, or amphotericin B.

* * * * *